US012656355B2

(12) United States Patent (10) Patent No.: US 12,656,355 B2
Lenhert et al. (45) Date of Patent: Jun. 16, 2026

(54) TWO PHASE INDICATOR DISPLACEMENT ASSAY

(71) Applicant: The Florida State University Research Foundation, Inc., Tallahassee, FL (US)

(72) Inventors: Steven Lenhert, Tallahassee, FL (US); Emily Shiel, Tallahassee, FL (US); Huanhuan Zhou, Tallahassee, FL (US)

(73) Assignee: The Florida State University Research Foundation, Inc., Tallahassee, FL (US)

( * ) Notice: Subject to any disclaimer, the term of this patent is extended or adjusted under 35 U.S.C. 154(b) by 568 days.

(21) Appl. No.: 18/133,651

(22) Filed: Apr. 12, 2023

(65) Prior Publication Data

US 2023/0333127 A1 Oct. 19, 2023

Related U.S. Application Data

(60) Provisional application No. 63/330,970, filed on Apr. 14, 2022.

(51) Int. Cl.
*G01N 21/64* (2006.01)
*B01L 3/00* (2006.01)
(Continued)

(52) U.S. Cl.
CPC ........ *G01N 33/92* (2013.01); *B01L 3/502715* (2013.01); *C23C 2/51* (2022.08); (Continued)

(58) Field of Classification Search
CPC .. G01N 33/92; G01N 21/77; B01L 3/502715; B01L 2200/0694; B01L 2200/16; B01L 2300/0636; C23C 2/51; A61M 2205/3303
See application file for complete search history.

(56) References Cited

U.S. PATENT DOCUMENTS 6,306,598 B1 * 10/2001 Charych ................ B82Y 15/00
422/67

FOREIGN PATENT DOCUMENTS

WO WO-2015066740 A1 * 5/2015 ........... G01N 31/221

OTHER PUBLICATIONS

Zhong, Chunting, et al. "Cucurbit [n] uril-immobilized sensor arrays for indicator-displacement assays of small bioactive metabolites." ACS Applied Nano Materials 4.5 (2021): 4676-4687. (Year: 2021).*

(Continued)

*Primary Examiner* — Jennifer Wecker
*Assistant Examiner* — Oyeleye Alexander Alabi
(74) *Attorney, Agent, or Firm* — Meunier Carlin & Curfman LLC

(57) ABSTRACT

The present disclosure provides for a method of detecting the displacement of a specific analyte, including providing an indicator in an organic phase to form a first composition; providing an aqueous phase with a test analyte to form a second composition; adding at least one organic solute to the organic phase; putting the first composition and second composition in contact with each other, thereby forming a lamellar phase and an interface between the first composition and second composition; and detecting the presence of the indicator in the organic phase, wherein the presence of the indicator in the organic phase indicates the presence of the specific analyte. The present disclosure also provides for a method of developing a high throughput assay for contemporaneous detection of multiple analytes. Further, the present disclosure provides for a biosensor for detection of a specific analyte.

20 Claims, 11 Drawing Sheets

(51) Int. Cl.

| | |
|---|---|
| *B82Y 5/00* | (2011.01) |
| *B82Y 30/00* | (2011.01) |
| *B82Y 40/00* | (2011.01) |
| *C07F 5/02* | (2006.01) |
| *C09B 57/00* | (2006.01) |
| *C09K 11/06* | (2006.01) |
| *C23C 2/00* | (2006.01) |
| *G01N 1/30* | (2006.01) |
| *G01N 15/10* | (2024.01) |
| *G01N 15/1429* | (2024.01) |
| *G01N 27/626* | (2021.01) |
| *G01N 31/22* | (2006.01) |
| *G01N 33/483* | (2006.01) |
| *G01N 33/543* | (2006.01) |
| *G01N 33/58* | (2006.01) |
| *G01N 33/68* | (2006.01) |
| *G01N 33/92* | (2006.01) |

(52) U.S. Cl.
CPC .................. *A61M 2205/3303* (2013.01); *B01L 2200/0694* (2013.01); *B01L 2200/16* (2013.01); *B01L 2300/0636* (2013.01)

(56) References Cited

OTHER PUBLICATIONS

Ueda et al., "Liquid-Liquid Extraction of Basic Yellow 28, Basic Blue 41, and Basic Red 46 Dyes from Aqueous Solutions with Reverse Micelles," Journal of Chemical & Engineering Data, Jan. 2011, vol. 56, pp. 652-657.

Fontell et al., "Phase equilibria and structures in ternary systems of a cationic surfactant (C16 TABr or (C16 TA)2SO4), alcohol, and water," Colloid and Polymer Science, Jul. 1991, vol. 269, pp. 727-742.

Zhong et al., "Cucurbit[n]uril-Immobilized Sensor Arrays for Indicator-Displacement Assays of Small Bioactive Metabolites," ACS Applied Nano Materials, Mar. 2021, vol. 4, pp. 4676-4687.

Bajerski et al., "ATP Content and Cell Viability as Indicators for Cryostress Across the Diversity of Life," Frontiers in Physiology, Jul. 2018, vol. 9, No. 921, pp. 1-14.

Tian et al., "Detection of Viable Bacteria during Sludge Ozonation by the Combination of ATP Assay with PMA-Miseq Sequencing," Water, Feb. 2017, vol. 9, No. 166, pp. 1-12.

Crouch et al., "The use of ATP bioluminescence as a measure of cell proliferation and cytotoxicity," Journal of Immunological Methods, 1993, vol. 160, No. 1, pp. 81-88.

Herrera et al., "Rapid Optical Determination of Enantiomeric Excess, Diastereomeric Excess, and Total Concentration Using Dynamic-Covalent Assemblies: A Demonstration Using 2-Aminocyclohexanol and Chemometrics," Author Manuscript, Journal of the American Chemical Society, Jul. 2019, vol. 141, No. 28, pp. 11151-11160.

Sedgwick et al., "Indicator displacement assays (IDAs): the past, present and future," Chemical Society Reviews, Jan. 2021, vol. 50, No. 1, pp. 9-38.

Mitchell et al., "Macromolecular Optical Sensor Arrays," ACS Applied Polymer Materials, Jan. 2021, vol. 3, No. 2, pp. 506-530.

Zhang et al., "Liquid-liquid phase separation in biology: mechanisms, physiological functions and human diseases," Science China Life Sciences, Jul. 2020, vol. 63, No. 7, pp. 953-985.

Peng et al., "From start to end: Phase separation and transcriptional regulation," Biochimica et Biophysica Acta (BBA)-Gene Regulatory Mechanisms, Dec. 2020, vol. 1863, No. 12, 194641.

O'Flynn et al., "The role of liquid-liquid phase separation in regulating enzyme activity," Author Manuscript, Current Opinion in Cell Biology, Apr. 2021, vol. 69, pp. 70-79.

Alberti, Simon, "Phase separation in biology," Current Biology, Oct. 2017, vol. 27, pp. R1097-R1102.

Hyman et al., "Liquid-liquid phase separation in biology," Annual Review Of Cell And Developmental Biology, Oct. 2014, vol. 30, pp. 39-58.

Blaker et al., "Novel fabrication techniques to produce microspheres by thermally induced phase separation for tissue engineering and drug delivery," Acta Biomaterialia, Mar. 2008, vol. 4, No. 2, pp. 264-272.

Boeynaems et al., "Protein Phase Separation: A New Phase in Cell Biology," Author Manuscript, Trends in Cell Biology, Jun. 2018, vol. 28, No. 6, pp. 420-435.

Entezari et al., "Phase-transfer catalysis and ultrasonic waves II: saponification of vegetable oil," Ultrasonics Sonochemistry, Jul. 2001, vol. 8, No. 3, pp. 213-216.

Bell et al., "Organic Composomes as Supramolecular Aptamers." ACS Omega, 2020, vol. 5, No. 42, pp. 27393-27400.

Rowland et al., "Kinetics of drug-drug interactions," Journal of Pharmacokinetics and Biopharmaceutics, 1973, vol. 1, pp. 553-567.

Zeyda et al., "LAT displacement from lipid rafts as a molecular mechanism for the inhibition of T cell signaling by polyunsaturated fatty acids," Journal of Biological Chemistry, Aug. 2002, vol. 277, No. 32, pp. 28418-28423.

Yan et al., "Specificity quantification of biomolecular recognition and its implication for drug discovery," Scientific Reports, Mar. 2012, vol. 2, No. 309, pp. 1-7.

Vazquez et al., "From transcription factors to designed sequence-specific DNA-binding peptides," Chemical Society Reviews, Jul. 2003, vol. 32, No. 6, pp. 338-349.

Babine et al., "Molecular Recognition of Protein-Ligand Complexes: Applications to Drug Design," Chem. Rev. 1997, vol. 97, No. 5, pp. 1359-1472.

Zhou et al., "Specific Noncovalent Interactions at Protein-Ligand Interface: Implications for Rational Drug Design," Current Medicinal Chemistry, 2012, vol. 19, No. 2, pp. 226-238.

Segré et al., "The Lipid World," Origins of Life and Evolution of the Biosphere, 2001, vol. 31, pp. 119-145.

Kahana et al., "Dynamic lipid aptamers: non-polymeric chemical path to early life," Chemical Society Review, Sep. 2021, vol. 50, No. 21, pp. 11741-11746.

Kahana et al., "Self-reproducing catalytic micelles as nanoscopic protocell precursors," Nature Reviews Chemistry, Oct. 2021, vol. 5, No. 12, pp. 870-878.

Klein et al., "Partitioning of cancer therapeutics in nuclear condensates," Science, Jun. 2020, vol. 368, No. 6497, pp. 1386-1392.

Hilt et al., "Configurational biomimesis in drug delivery: molecular imprinting of biologically significant molecules," Advanced Drug Delivery Reviews, Sep. 2004, vol. 56, No. 11, pp. 1599-1620.

Yang et al., "Biomacromolecular nanostructures-based interfacial engineering: from precise assembly to precision biosensing," National Science Review, Feb. 2018, vol. 5, No. 5, pp. 740-755.

Selvi et al., "The Basic Principle of Phase-Transfer Catalysis, Some Mechanistic Aspects and Important Applications," International Journal of Scientific & Technology Research, Apr. 2012, vol. 1, No. 3, pp. 61-63.

Makosza et al., "Phase Transfer Catalysis—Basic Principles, Mechanism and Specific Features," Current Catalysis, 2012, vol. 1, No. 2, pp. 79-87.

Makosza, M., "Phase-transfer catalysis. A general green methodology in organic synthesis," Pure and Applied Chemistry, Jan. 2000, vol. 72, No. 7, pp. 1399-1403.

Godha et al., "Environmentally benign nucleophilic substitution reaction of arylalkyl halides in water using CTAB as the inverse phase transfer catalyst," New Journal of Chemistry, Sep. 2019, vol. 43, No. 40, pp. 16041-16045.

Ellington et al., "In vitro selection of RNA molecules that bind specific ligands," Nature, Aug. 1990, vol. 346, pp. 818-822.

Henchman et al., "Asymmetric Structural Motions of the Homomeric α7 Nicotinic Receptor Ligand Binding Domain Revealed by Molecular Dynamics Simulation," Biophysical Journal, Nov. 2003, vol. 85, No. 5, pp. 3007-3018.

Ivanov et al., "Molecular dynamics simulation of the P2Y14 receptor. Ligand docking and identification of a putative binding site of the distal hexose moiety," Author Manuscript, Bioorganic & Medicinal Chemistry Letters, Feb. 2007, vol. 17, No. 3, pp. 761-766.

(56)          References Cited

OTHER PUBLICATIONS

Rakers et al., "Computational close up on protein-protein interactions: how to unravel the invisible using molecular dynamics simulations?" Wiley Interdisciplinary Reviews: Computational Molecular Science, 2015, vol. 5, No. 5, pp. 345-359.

Reynwar et al., "Membrane composition-mediated protein-protein interactions," Biointerphases, Jun. 2008, vol. 3, No. 2, pp. FA117-FA124.

Chavent et al., "Molecular dynamics simulations of membrane proteins and their interactions: from nanoscale to mesoscale," Current Opinions in Structural Biology, Oct. 2016, vol. 40, pp. 8-16.

Pluhackova et al., "A Critical Comparison of Biomembrane Force Fields: Structure and Dynamics of Model DMPC, POPC, and POPE Bilayers," The Journal of Physical Chemistry B, Apr. 2016, vol. 120, No. 16, pp. 3888-3903.

Zhuang et al., "An extensive simulation study of lipid bilayer properties with different head groups, acyl chain lengths, and chain saturations," Biochimica et Biophysica Acta, Dec. 2016, vol. 1858, No. 12, pp. 3093-3104.

Kikkawa et al., "Molecular dynamics study of phase transfer catalyst for ion transfer through water-chloroform interface," Chemical Physics Letters, May 2012, vol. 534, pp. 19-22.

Melville et al., "Exploring Phase-Transfer Catalysis with Molecular Dynamics and 3D/4D Quantitative Structure-Selectivity Relationships," Journal of Chemical Information and Modeling, May 2005, vol. 45, No. 4, pp. 971-981.

Oberbrodhage, J., "Phase transfer catalysts between polar and non-polar media: a molecular dynamics simulation of tetrabutylammonium iodide at the formamide/hexane interface," Physical Chemistry Chemical Physics, 2000, vol. 2, pp. 129-135.

Jang et al., "Thermal and mechanical properties of thermosetting polymers using coarse-grained simulation," The European Physical Journal Special Topics, Jul. 2016, vol. 225, No. 8-9, pp. 1775-1783.

Lopez et al., "Martini Coarse-Grained Force Field: Extension to Carbohydrates," Journal of Chemical Theory and Computation, Oct. 2009, vol. 5, pp. 3195-3210.

Marrink et al., "The Martini Force Field: Coarse Grained Model for Biomolecular Simulations," The Journal of Physical Chemistry B, Jun. 2007, vol. 111, pp. 7812-7824.

Lin et al., "Understanding selective molecular recognition in integrated carbon nanotube-polymer sensors by simulating physical analyte binding on carbon nanotube-polymer scaffolds," Accepted Manuscript, Soft Matter, Jun. 2014, vol. 10, No. 32, pp. 5991-6004.

Uusitalo et al., "Martini Coarse-Grained Force Field: Extension to DNA," Journal of Chemical Theory and Computation, Jul. 2015, vol. 11, No. 8, pp. 3932-3945.

Uusitalo et al., "Martini Coarse-Grained Force Field: Extension to RNA," Biophysical Journal, Jul. 2017, vol. 113, No. 2, pp. 246-256.

Monitcelli et al., "The Martini Coarse-Grained Force Field: Extension to Proteins," Journal of Chemical Theory and Computation, Apr. 2008, vol. 4, pp. 819-834.

Alessandri et al., "Martini 3 Coarse-Grained Force Field: Small Molecules," Advanced Theory and Simulations, 2021, vol. 5, pp. 1-19.

Hinner et al., "Location, Tilt, and Binding: A Molecular Dynamics Study of Voltage-Sensitive Dyes in Biomembranes," Journal of Physical Chemistry B, Nov. 2009, vol. 113, No. 48, pp. 15807-15819.

"Resonance," IUPAC-compendium-of-chemical-terminology (the Gold Book) 2006, Online corrected version.

Thornburg, W., "The form birefringence of lamellar systems containing three or more components," The Journal Of Biophysical And Biochemical Cytology, 1957, vol. 3, No. 3, pp. 413-419.

Mashaghi et al., "Optical Anisotropy of Supported Lipid Structures Probed by Waveguide Spectroscopy and Its Application to Study of Supported Lipid Bilayer Formation Kinetics," Analytical Chemistry, May 2008, vol. 80, pp. 3666-3676.

Javanainen et al., "Anisotropic diffusion of membrane proteins at experimental timescales," The Journal of Chemical Physics, Jul. 2021, vol. 155, No. 1, 015102-1-015102-14.

Mahamid et al., "Liquid-crystalline phase transitions in lipid droplets are related to cellular states and specific organelle association," PNAS, Aug. 2019, vol. 116, No. 34, pp. 16866-16871.

Streck et al., "Phase Transitions of Isotropic to Anisotropic Biocompatible Lipid-Based Drug Delivery Systems Overcoming Insoluble Benznidazole Loading," International Journal of Molecular Science, Jun. 2016, vol. 17, No. 7, pp. 1-18.

Lowry et al., "Odor Discrimination by Lipid Membranes," Membranes, Jan. 2023, vol. 13, pp. 1-12.

Sago et al., "Nanoparticles That Deliver RNA to Bone Marrow Identified by in Vivo Directed Evolution," Author Manuscript, Journal of the American Chemical Society, Dec. 2018, vol. 140, No. 49, pp. 17095-17105.

Thompson et al., "LAMMPS—a flexible simulation tool for particle-based materials modeling at the atomic, meso, and continuum scales," Computer Physics Communications, Feb. 2022, vol. 271, 108171, 34 pages.

Best et al., "Free Energy Perturbation Study of Octanol/Water Partition Coefficients: Comparison with Continuum GB/SA Calculations," The Journal of Physical Chemistry B, Jan. 1999, vol. 103, pp. 714-726.

Van Gunsteren et al., "Thermodynamic cycle integration by computer simulation as a tool for obtaining free energy differences in molecular chemistry," Journal of Computer-Aided Molecular Design, Aug. 1987, vol. 1, pp. 171-176.

* cited by examiner

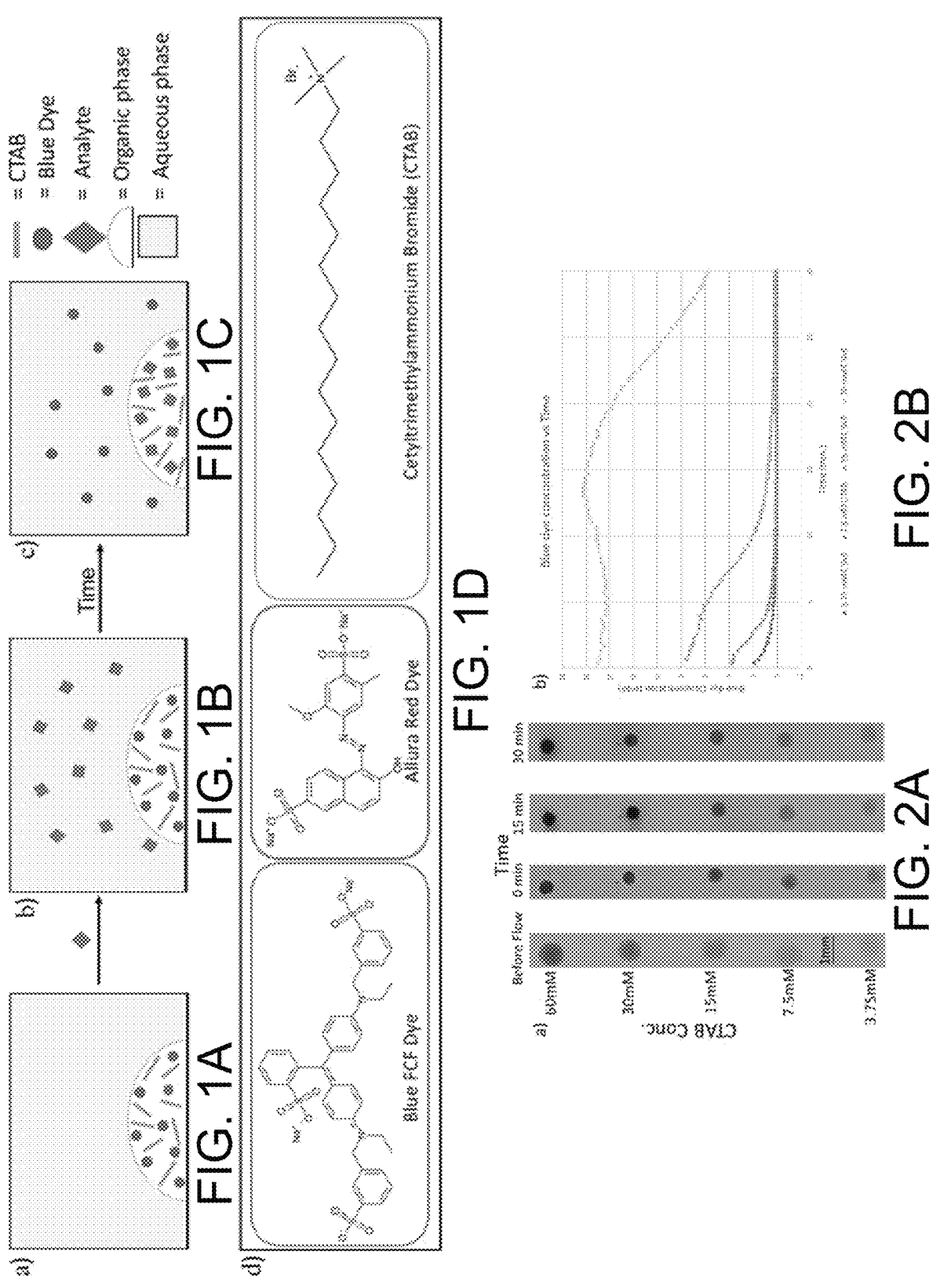

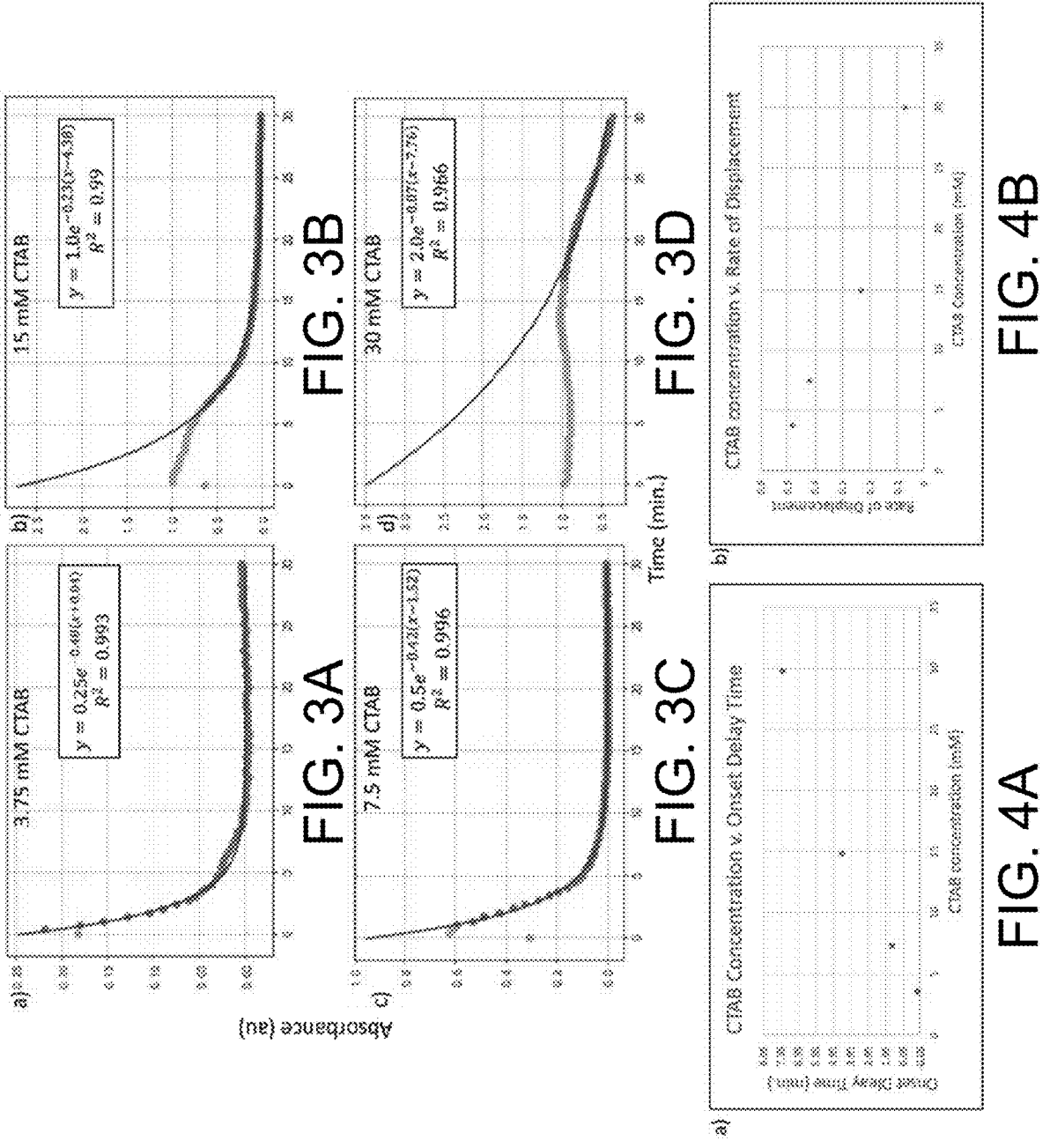

(a)　100 CTAB (b)　300 CTAB (c)　500 CTAB (d)　700 CTAB (e)　1000 CTAB

Red dyes being trapped at the multilayer structure

Multilayer structure formed by CTAB at high concentration

FIG. 15A                    FIG. 15B

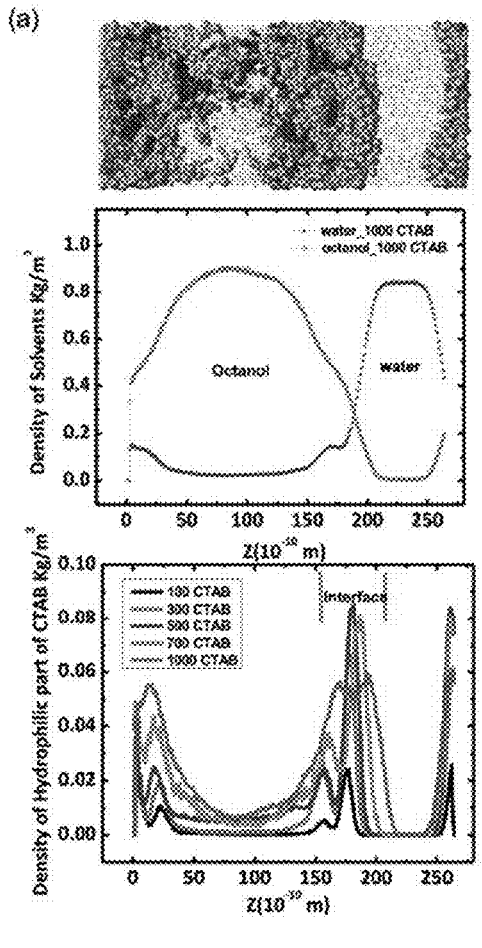
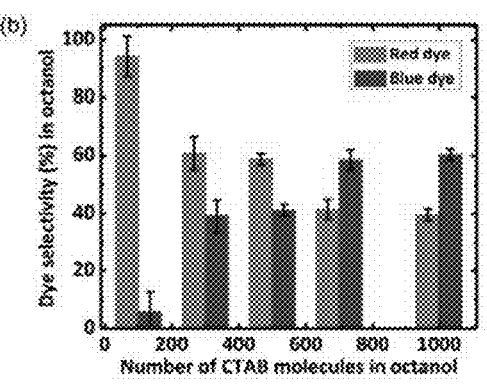
FIG. 21B
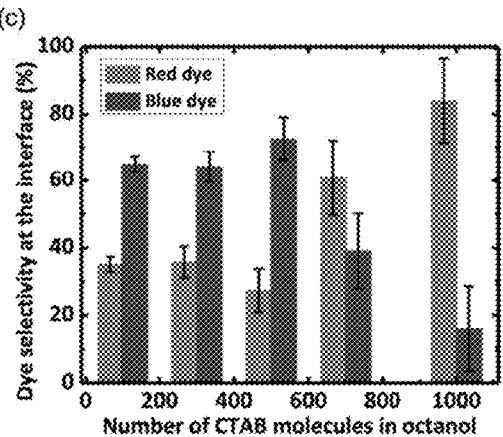
FIG. 21A          FIG. 21C
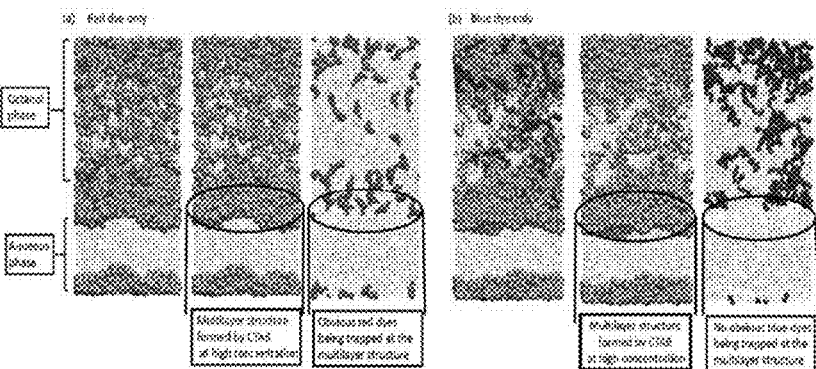          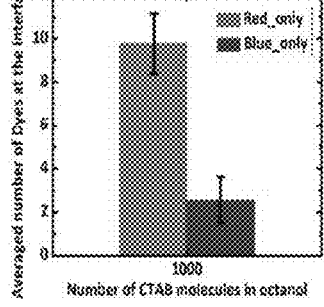
FIG. 22A          FIG. 22B          FIG. 22C

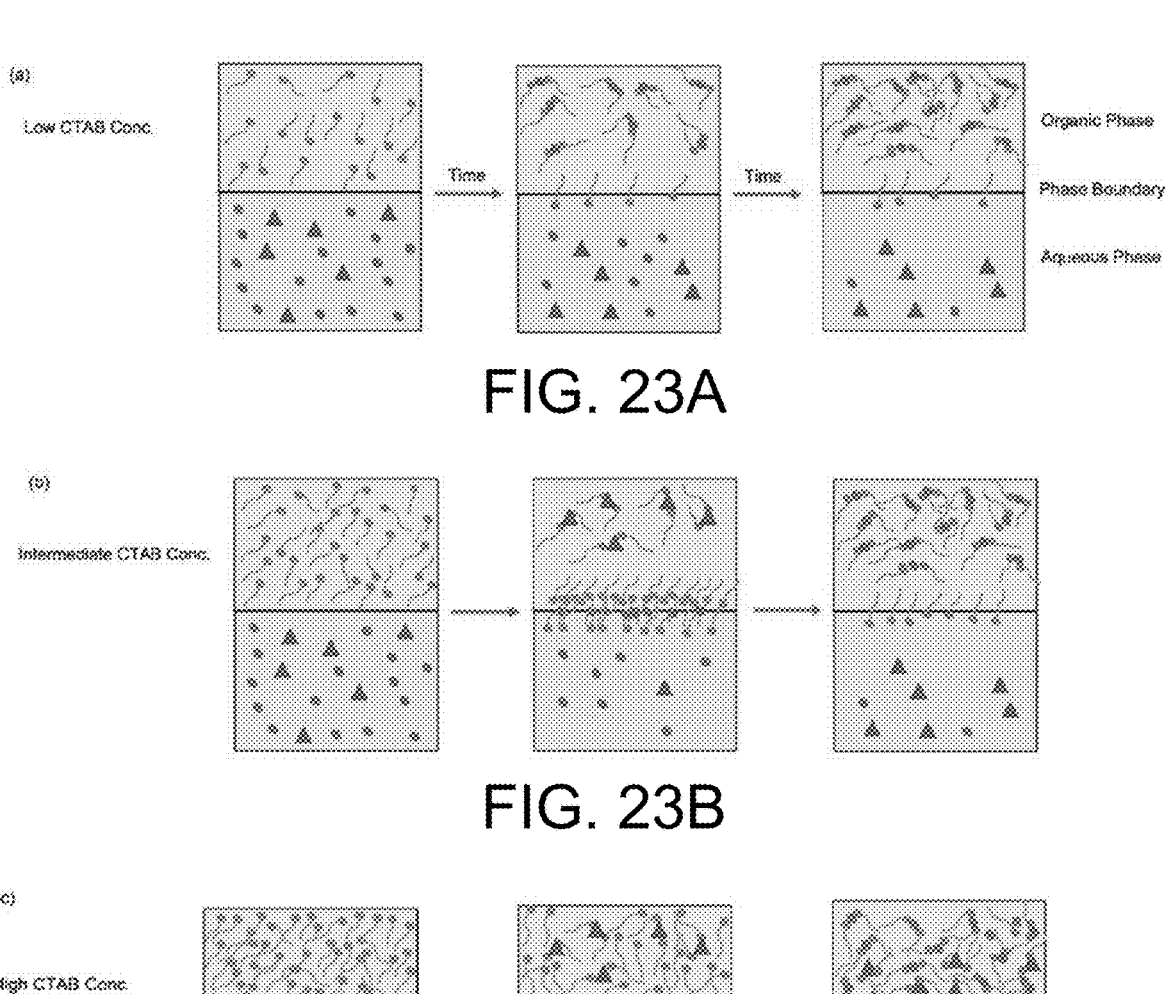
FIG. 23A
FIG. 23B
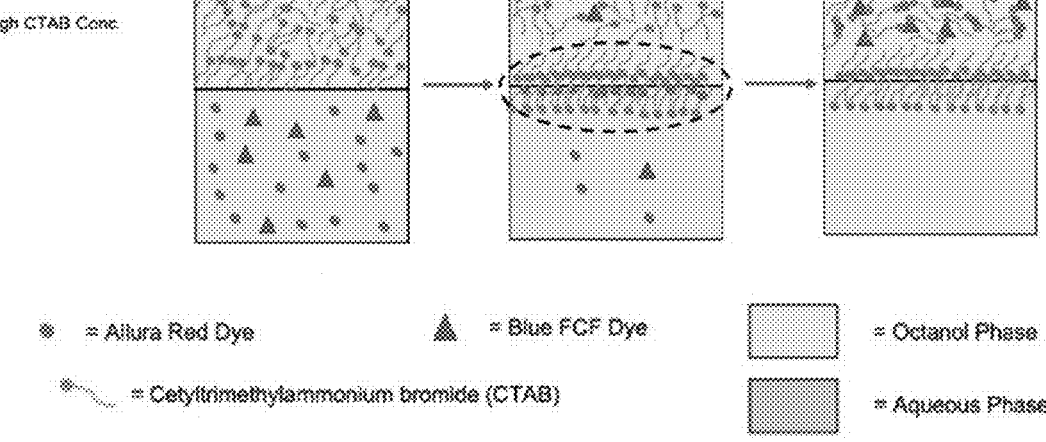
FIG. 23C

TWO PHASE INDICATOR DISPLACEMENT ASSAY

CROSS-REFERENCE TO RELATED APPLICATIONS

This application claims the benefit of priority to U.S. Patent Application No. 63/330,970 filed on Apr. 14, 2022, the disclosure of which is expressly incorporated by reference herein in its entirety.

BACKGROUND

Biosensors are developed with the aim of detecting the presence of a target molecule within a certain solution or medium. Within the past few decades, many biosensors revolved around a design involving supramolecular-based molecular sensors, otherwise known as indicator displacement assays (IDAs). These IDAs generally consist of a supramolecular assembly which includes an optical indicator that is reversibly bound to a synthetic receptor. In the presence of an analyte, the optical indicator would be displaced from the synthetic receptor resulting in an optical signal. These IDAs have proven to have many effective applications in the fields of industrial, agriculture, environmental, and biological sciences. Additionally, indicator displacement can be used to detect binding in biochemical assays. (Sedgwick et al.; Mitchell L. et al.) However, there are still many limitations that need to be surmounted if the full capability of this technique is to be recognized. Some of these limitations include low signal-to-noise ratio and sensitivity of IDAs. (Sedgwick et al.)

The methods and devices described herein addresses these and other needs.

SUMMARY

In accordance with the purposes of the disclosed materials and methods, as embodied and broadly described herein, the present disclosure relates to a method of detecting the presence of a specific analyte, a method of developing a high throughput assay for contemporaneous detection of multiple analytes, and a biosensor for detection of a specific analyte.

Thus, in one aspect, provided herein is a method of detecting the displacement of a specific analyte, including providing an indicator in an organic phase to form a first composition; providing an aqueous phase with a test analyte to form a second composition; adding at least one organic solute to the organic phase; putting the first composition and second composition in contact with each other, thereby forming a lamellar phase and an interface between the first composition and second composition; and detecting the presence of the indicator in the organic phase, wherein the presence of the indicator in the organic phase indicates the presence of the specific analyte.

In an additional aspect, provided herein is a method of developing a high throughput assay for contemporaneous detection of multiple analytes, the method including providing an indicator in an organic phase to form a first composition; providing an aqueous phase with a test analyte to form a second composition; adding organic solute to the organic phase; putting the first composition and second composition in contact with each other, thereby forming a lamellar phase and an interface between the first composition and second composition; detecting the presence of the indicator in the organic phase, wherein the displacement of the indicator in the organic phase indicates the presence of the specific analyte; and repeating steps a-e for multiple analytes, wherein a computer system is used to analyze and store data regarding chemical kinetics of each analyte, thereby creating individual profiles for each analyte which can be used in a high throughput assay to detect multiple analytes contemporaneously.

In a further aspect, provided herein is a biosensor for detection of a specific analyte, wherein the biosensor includes an organic droplet inside of an aqueous phase; an indicator dissolved in an organic phase; and a lamellar phase, wherein said aqueous phase includes a test analyte, and further wherein said indicator moves from the organic phase to the aqueous phase in the presence of the specific analyte.

Herein, the indicator can be displaced from one phase into another. The indicator can be dissolved in the organic phase and an analyte can be added into an aqueous phase. The analyte can displace the indicator from the organic phase into the aqueous phase, allowing for analyte detection. This approach utilizes complex and dynamic supramolecular receptors that may transiently form in the organic phase or at the interface. (Bell et al.) This type of displacement assay can be referred to as a partitioning indicator displacement assay (PIDA). Lipid droplets arrays can be made based on the optimal material. First steps can be taken to apply this technology to large molecules such as DNA. A general sensor can use the provided method to selectively detect molecules by using a combinatorial material. The concept of displacement is particularly important in pharmacology, where drug binding proteins in the blood can sequester drugs making them less bioavailable. Understanding displacement aids in understanding drug interactions, as taking a second drug can displace the first drug from drug binding proteins, thus leading to toxicity that would not be observed at the dosage of a single drug. This mechanism also has implications in biological systems, where small molecules may be displaced from nonpolar condensates such as lipid bilayers, lipid droplets, or other phase separated compartments. (Hyman et al.) Phase separation plays a role in regulation of enzymatic activity, gene expression, higher order chromatin organization, and the breakdown of misfolded proteins. (Zhang et al., Peng et al.; O'Flynn et al.; Alberti et al.).

Additional advantages will be set forth in part in the description that follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF FIGURES

The accompanying figures, which are incorporated in and constitute a part of this specification, illustrate several aspects described below.

FIGS. 1A-1D show an exemplary schematic of a two phase sensor and chemical structures. In FIG. 1A, an indicator is only present in the organic phase. In FIG. 1B, an analyte is added to aqueous phase. In FIG. 1C, analyte partitions into organic phase displacing the indicator. FIG. 1D shows chemical structures of two analytes, indicator, and two phase sensor components.

FIGS. 2A-2B show blue dye displacement by red dye at different CTAB concentrations. FIG. 2A shows images showing blue dye being displaced by red dye at various CTAB concentrations over time. FIG. 2B is a graph showing blue dye concentration over time at the various CTAB concentrations.

FIGS. 3A-3D show that delay in onset of displacement is proportional to CTAB concentration. Calculated displacement equations for different concentrations used in the PIDA with a blue 1 dye indicator and a red 40 dye analyte are shows in FIGS. 3A-3D. Displacement equation fitting for 3.75 mM (FIG. 3A), 15 mM (FIG. 3B), 7.5 mM (FIG. 3C), and 30 mM (FIG. 3D) are shown.

FIGS. 4A-4B show the data from the displacement equations in FIGS. 3A-3D. FIG. 4A shows a graph showing onset delay time versus CTAB concentration. FIG. 4B shows a graph showing rate of displacement versus CTAB concentration.

FIG. 1 at different CTAB concentrations over time.

FIGS. 15A-15B show experimental setup of the surfactant mediated selective partitioning studied here. (a) Chemical structures of CTAB and the blue and red dyes used in this system. CTAB has a net charge of +1 and the dyes have net charges of −2. (b) Liquid-liquid extraction setup. Initially, CTAB is dissolved in the organic phase (octanol), and the dyes are dissolved in the water. The dyes then transfer into the organic phase.

FIGS. 21A-21C shows quantification of the distribution of molecules between the two phases in the simulation. Density profiles along the z direction of the simulation box for octanol and water phase for all CTAB concentrations used in the simulations are shown in (a). In (a), water_1000 means the water density profile when the number of CTAB in octanol is 1000. Octanol_100 means the octanol density profile when the number of CTAB in octanol is 1000. Herein, z was from 20 angstrom (Å) to 130 Å as the octanol phase, z from 150 Å to 200 Å as the interface, and calculated dye selectivity of both dyes over the last 300 ns, which include 100 simulation frames and the interval between each frame is 3 ns. The error bars represent the standard deriva-tion of the selectivity of both dyes (b) in the octanol and (d) at the interface. (c) shows the density profile for the hydro-philic part of CTAB along z direction.

FIGS. 22A-22C shows testing of the hypothesis that red dye preferentially partitions into the CTAB lamellar phase at the interface at high CTAB concentrations as a mechanism for selective partitioning kinetics. (a) red dye only and (b) blue dye only at high CTAB concentration. The system contains 10000 CG water molecules (yellow beads), 10000 CG octanol molecules (orange beads), 60 CG red dye molecules (red beads), 60 CG blue dye molecules (blue beads) and 1000 CG CTAB molecules (cyan beads represent the hydrophilic part, green beads represent the hydrophobic part). There are three snapshots in (a), the first one showing all chemicals, the second one only showing CTAB, and third one only showing both dyes in water and octanol. And similarly, applied to (b). (c) shows the average number of red dye at the interface in (a) and blue dyes at the interface in (b) over the last 300 ns.

FIGS. 23A-23C is a schematic of the mechanism in (a) low, (b) intermediate, and (c) high CTAB concentration with blue and red dry partitioning. In the region marked with solid dash line at the water-octanol interface, there is a multilayer structure formed where red dye is trapped. This multilayer structure is referred to as a "supramolecular aptamer".

DETAILED DESCRIPTION

Figures 5, 6A, 6B:
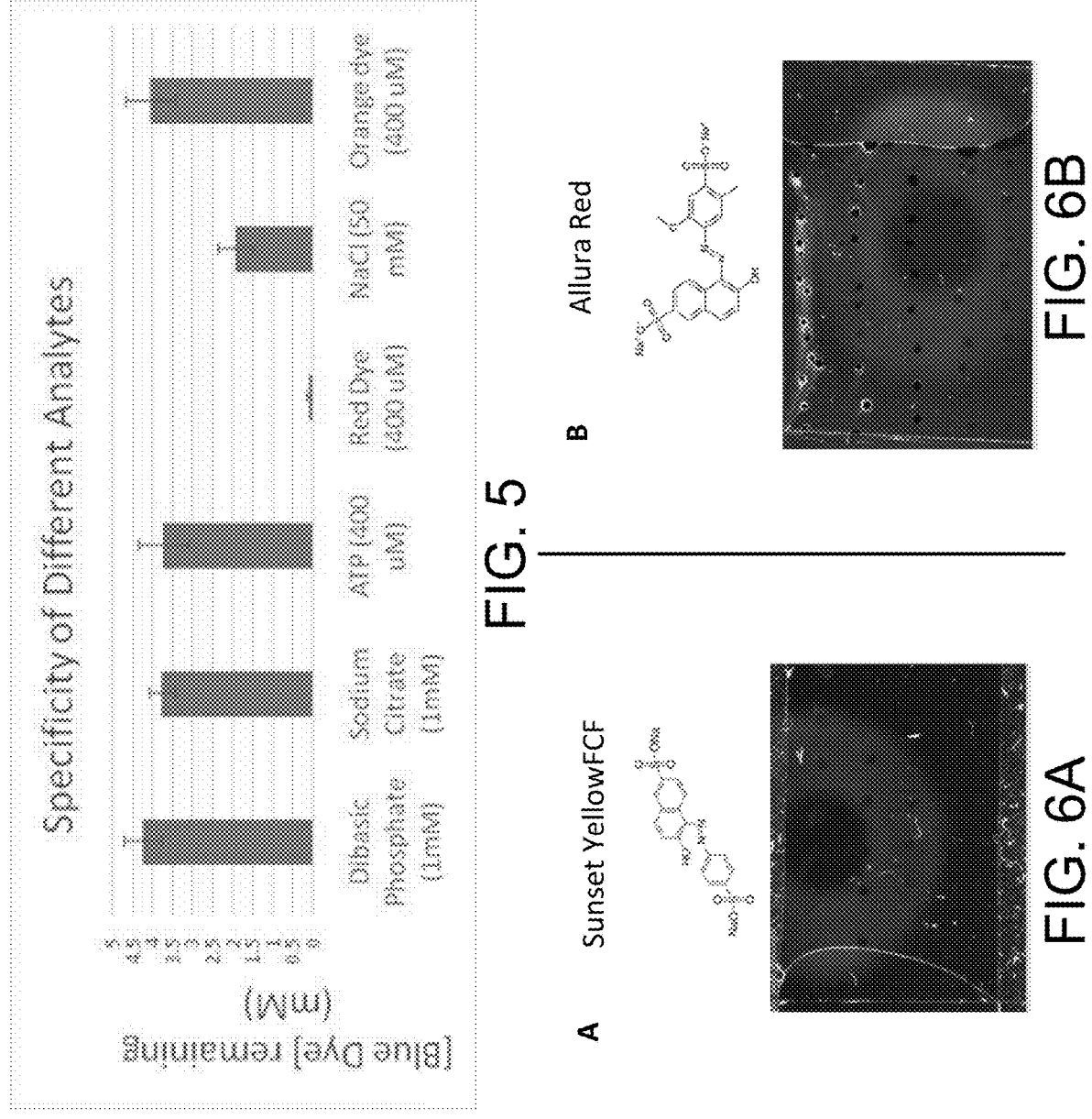
FIG. 5 shows the specificity of Partitioning Indicator Displacement Assay (PIDA) using 7.5 mM CTAB containing octanol drops and blue 1 FCF dye indicator. The figure shows the concentration of blue 1 FCF dye remaining in CTAB containing organic drops 10 minutes after the addition of analyte flow for six different analytes.
FIGS. 6A-6B show crossed polarizer images of arrays showing a birefringent phase forming when CTAB containing droplets are exposed to Allura Red dye, but not a similar compound, Sunset Yellow FCF, which indicates selectivity.

The following description of the disclosure is provided as an enabling teaching of the disclosure in its best, currently known embodiments. Many modifications and other embodiments disclosed herein will come to mind to one skilled in the art to which the disclosed compositions and methods pertain having the benefit of the teachings pre-sented in the foregoing descriptions and the associated drawings. Therefore, it is to be understood that the disclo-sures are not to be limited to the specific embodiments disclosed and that modifications and other embodiments are intended to be included within the scope of the appended claims. The skilled artisan will recognize many variants and adaptations of the aspects described herein. These variants and adaptations are intended to be included in the teachings of this disclosure and to be encompassed by the claims herein.

Although specific terms are employed herein, they are used in a generic and descriptive sense only and not for purposes of limitation.

As can be apparent to those of skill in the art upon reading this disclosure, each of the individual embodiments described and illustrated herein has discrete components and features which may be readily separated from or combined with the features of any of the other several embodiments without departing from the scope or spirit of the present disclosure.

Any recited method can be carried out in the order of events recited or in any other order that is logically possible. That is, unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including mat-ters of logic with respect to arrangement of steps or opera-tional flow, plain meaning derived from grammatical orga-nization or punctuation, or the number or type of aspects described in the specification.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admis-sion that the present invention is not entitled to antedate such publication by virtue of prior invention. Further, the dates of publication provided herein can be different from the actual publication dates, which can require independent confirma-tion.

It is also to be understood that the terminology used herein is for the purpose of describing particular aspects only and is not intended to be limiting. Unless defined otherwise, all technical and scientific terms used herein have the same meaning as commonly understood by one of ordinary skill in the art to which the disclosed compositions and methods belong. It can be further understood that terms, such as those defined in commonly used dictionaries, should be inter-preted as having a meaning that is consistent with their meaning in the context of the specification and relevant art and should not be interpreted in an idealized or overly formal sense unless expressly defined herein.

Prior to describing the various aspects of the present disclosure, the following definitions are provided and should be used unless otherwise indicated. Additional terms may be defined elsewhere in the present disclosure.

Definitions

As used herein, "comprising" is to be interpreted as specifying the presence of the stated features, integers, steps, or components as referred to, but does not preclude the presence or addition of one or more features, integers, steps, or components, or groups thereof. Moreover, each of the terms "by", "comprising," "comprises", "comprised of," "including," "includes," "included," "involving," "involves," "involved," and "such as" are used in their open, non-limiting sense and may be used interchangeably. Fur-ther, the term "comprising" is intended to include examples and aspects encompassed by the terms "consisting essen-tially of" and "consisting of." Similarly, the term "consisting essentially of" is intended to include examples encompassed by the term "consisting of."

As used in the specification and the appended claims, the singular forms "a," "an" and "the" include plural referents unless the context clearly dictates otherwise. Thus, for example, reference to "a compound", "a composition", or "a disorder", includes, but is not limited to, two or more such compounds, compositions, or disorders, and the like.

It should be noted that ratios, concentrations, amounts, and other numerical data can be expressed herein in a range format. It can be further understood that the endpoints of each of the ranges are significant both in relation to the other endpoint, and independently of the other endpoint. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a numerical range of "0.1% to 5%" should be interpreted to include not only the explicitly recited values of 0.1% to 5%, but also include individual values (e.g., 1%, 2%, 3%, and 4%) and the sub-ranges (e.g., 0.5% to 1.1%; 5% to 2.4%; 0.5% to 3.2%, and 0.5% to 4.4%, and other possible sub-ranges) within the indicated range.

As used herein, "analyte" refers to the analyte being measured in the methods and devices disclosed herein. Exemplary analytes of interest are further described herein.

As used herein, "organic phase" refers to the non-aqueous phase of an at least biphasic mixture.

As used herein, "aqueous phase" refers to the homogeneous part of a heterogenous system, wherein the aqueous phase includes water.

As used herein, "lamellar phase" refers to sheets of bilayers separated by bulk liquid, wherein the bilayers include packed polar-headed long chain nonpolar-tail molecules in an environment of bulk polar liquid.

As used herein, "organic solute" refers to an organic substance that can be dissolved in a solution by a solvent. Organic solutes can include, but are not limited to, benzene, propane, acetaldehyde, methanol, formamide, acetate, methylammonium, or any combination thereof.

As used herein, "red color 40", also referred to as "Allura Red", is a dark red synthetic dye made from petroleum. Red color 40 can be made by coupling diazotized 5-amino-4-methoxy-2-toluenesulfonic acid with 6-hydroxy-2-naphthalene sulfonic acid.

As used herein, "copper' refers to Cu metal and alloys containing Cu.

As used herein, "oleic acid" is a monosaturated omega-9 fatty acid that occurs naturally in various animal and vegetable fats and oil. It has the formula $C_{18}H_{34}O_2$.

As used herein, "phosphonic acid" is a phosphorous oxoacid that consists of a single pentavalent phosphorous covalently bound via single bonds to a single hydrogen and two hydroxy groups and via a double bond to an oxygen. It has the chemical formula $H_3PO_3$. It is a conjugate acid of a phosphonate and a tautomer of a phosphorous acid. Phosphonic acid can act as a fungicide.

As used herein, "rotation of polarized light" refers to the rotation of the orientation of the plane of polarization about the optical axis of linearly polarized light as it travel through a material.

As used herein, "absorbance" refers to optical density, which is the quantity of light absorbed by a solution. Absorbance can be measured using a spectrophotometer or microplate reader, which is an instrument that shines light of a specified wavelength through a sample and measures the amount of light that the sample absorbs.

As used herein, "fluorescence" is a type of electromagnetic spectroscopy that analyzed fluorescence from a sample. It includes using a beam of light, often an ultraviolet light, that excites the electrons in molecules of certain compounds and causes them to emit light, which can include visible light.

As used herein, "surfactant" is a surface active agent that modifies interfacial tension of water. Surfactants can have one lipophilic and one hydrophilic group or region in the molecule. Broadly, the group includes soaps, detergents, emulsifiers, dispersing and wetting agents, and several groups of antiseptics. More specifically, surfactants include steeryltriethanolamine, sodium lauryl sulfate, sodium taurocholate, laurylaminopropionic acid, lecithin, benzalkonium chloride, benzethonium chloride and glycerin monostearate; and hydrophilic polymers such as polyvinyl alcohol, polyvinylpyrrolidone, polyethyleneglycol (PEG), carboxymethylcellulose sodium, methylcellulose, hydroxymethylcellulose, hydroxyethylcellulose and hydroxypropylcellulose or alkyl glycosides. In some embodiments, a surfactant is a non-ionic surfactant (e.g., an alkyl glycoside surfactant). In some embodiments, a surfactant is an ionic surfactant.

As used herein, "cetyltrimethylammonium bromide", or "CTAB", is a cationic detergent with the formula $C_{19}H_{42}BrN$.

As used herein, "light source" includes excitation sources, such as lasers, LED, lamps, xenon arc, and mercury-vapor lamps, for example.

As used herein, "detector" refers to a device that detect the intensity of light produced from the light source as it travels through a substance. Detectors can be either single-channeled or multi-channeled. The single-channeled detector can only detect the intensity of one wavelength at a time, while the multi-channeled can detect the intensity of all wavelengths simultaneously.

As used herein, "microfluidic device" is a device with micro-channels in a material, such as glass, silicon, or a polymer like PDMS. One major application for microfluidic devices is the separation and sorting of different fluids or cell types.

Methods

Method of Detecting the Presence of a Specific Analyte

Provided herein is a method of detecting the displacement of a specific analyte, including providing an indicator in an organic phase to form a first composition; providing an aqueous phase with a test analyte to form a second composition; adding at least one organic solute to the organic phase; putting the first composition and second composition in contact with each other, thereby forming a lamellar phase and an interface between the first composition and second composition; and detecting the displacement of the indicator in the organic phase, wherein the displacement of the indicator from the organic phase indicates the presence of the specific analyte.

In further aspects, the indicator can include erioglaucine disodium salt.

In some aspects, detecting the analyte can further include measuring kinetics of the displacement of the analyte. In further aspects, chemical kinetics can include the decay constant, also referred to as displacement rate, or the delay in onset time. These kinetic properties can be dependent on the concentration of CTAB. (See FIGS. 4A-4B.)

In certain aspects, the method can further include determining analyte concentration based on selective partitioning rate of the indicator and analyte. As used herein, the selective partitioning rate can refer to the rate at which the indicator is displaced from the organic phase.

In some aspects, the method can further include arraying at least two analytes on a single object; and performing multiplexed detection. In further aspects, the method can further include arraying at least 3, at least 5, at least 10, at least 15, or at least 20 analytes on a single object. In certain aspects, the method can further include arraying from 2 to 5, 2 to 10, 2 to 15, or 2 to 20 analytes on a single object. In specific aspects, the method can further include arraying from 2 to 20, 5 to 20, 10 to 20, or 15 to 20 analytes on a single object.

In further aspects, adding organic solute to the organic phase can include dissolving the at least one organic solute in the organic phase.

In certain aspects, the analyte can include small molecules or ions. In certain aspects, the analyte can include red color 40. In specific aspects, the analyte can include copper.

In some aspects, the organic phase can include oleic acid. In further aspects, the organic phase can include fatty acids such as palmitic acid, elaidic acid, or vacentic acid. In certain aspects, the organic phase can include octanol, or more specifically, 1-octanol. In some aspects, the organic phase can include an additive. In specific aspects, the additive can include phosphonic acid. In further aspects, the additive can include carbonic acid, bicarbonate, methylglyoxal, nitrate, nitric acid, or any combination thereof.

In certain aspects, the aqueous phase can include a biological sample or environmental sample.

In some aspects, the organic phase can have a volume from 1 zeptoliter to 100 milliliters and the aqueous phase can have a volume from 100 nanoliters to 500 milliliters. Smaller organic phase droplets can lead to faster detection, higher sensitivity and lower limits of detection. The composition of the organic phase can allow for selectivity.

In further aspects, the method can further include measuring rotation of polarized light. Further, measuring rotation of polarized light can occur in the absence of an indicator.

In certain aspects, the indicator can be detected via absorbance, fluorescence, or any combination thereof.

In some aspects, the organic phase can be in the form of an organic droplet within the aqueous phase.

In further aspects, the organic solute can include at least one surfactant. In some aspects, the surfactant can include cetyltrimethylammonium bromide (CTAB).

In certain aspects, detecting the presence of the indicator in the organic phase can include applying a light source. In further aspects, detecting the presence of the indicator in the organic phase can include applying a detector.

In some aspects, the indicator and reagents used can be specific for the analyte, so that the indicator is displaced in the presence of the analyte. The indicator partitioned into the organic phase can be displaced by an analyte introduced into the aqueous phase, leading to label free detection of small molecules.

Biochemists have generally believed that molecular recognition was attributed to proteins and molecular recognition could not happen in vivo because biological lipids are generally thought to be fluid, fluids are thought to be disordered, and order is required for molecular recognition. It is generally emphasized that the selectivity comes from the membrane proteins and not the lipids. It is therefore very surprising to biologists or biochemists that collections of lipids or lipid-like molecules could show highly specific molecular recognition comparable to that of proteins. In particular, as disclosed herein, it is surprising that this system is so specific for Allura Red AC (red 40).

Further, a fundamental difference between the subject matter disclosed herein and the state of the art involves the sensing mechanism and structural mechanism. Displacement assays involve the binding of one molecule to another, not displacement from one phase to another. The subject matter disclosed herein involves displacement of an indicator from an organic phase into an aqueous phase, although displacement between a variety of phases and mesophases is envisioned.

It is structurally novel and surprising that the lamellar mesophase formed in between the organic and aqueous phases and was highly selective for the red dye. Other phases or phase transitions induced by the analyte become possible when one considers the mechanism described herein.

The use of the lamellar phase as a transduction mechanism is also novel. In addition to the displacement assay, the lamellar phase has unique optical properties that can be detected. Because it rotates polarized light, its formation can be detected by observation through crossed polarizers.

Furthermore, the specific nanostructures assembled could be used for assembly of new nanostructured devices capable of molecular recognition.

As a sensing platform, the formation of droplets as sensors is new and enabling in several ways. First, integration of droplets of different compositions can be generated, e.g., on a surface or in microfluidic devices. Droplets of different composition could be specific for different analytes allowing multiplexed detection. Smaller drops allow for faster sensing, higher sensitivity, and lower limits of detection.

Molecular recognition plays a role in enzymatic catalysis, and structures such as those formed in these sensors may be able to carry out selective or specific catalysis. This idea is thought to be impossible by many biochemists and molecular biologists who have thoroughly studied and unraveled protein-based pathways. The ability to selectively detect small molecules and ions is another property that is typically limited to proteins. The phase transitions observed in the molecular recognition can be used for drug delivery and release from carriers. Furthermore, the ability to carry out molecular recognition can result in biological activity of mixtures of lipid-like molecules that the individual components do not have. That is, mixtures of molecules in droplets could be a new type of drug-less drug. They can have immunomodulatory effects, or act as protein-free antibodies. The small molecule induction of a local phase transition can be used for mechanical actuation. The selectivity can be used for chemical separation and/or energy storage (e.g., electrolytes in batteries, or molecular storage and release for fuel cells).

Method of Developing a High Throughput Assay for Contemporaneous Detection of Multiple Analytes In an additional aspect, provided herein is a method of developing a high throughput assay for contemporaneous detection of multiple analytes, the method including providing an indicator in an organic phase to form a first composition; providing an aqueous phase with a test analyte to form a second composition; adding organic solute to the organic phase; putting the first composition and second composition in contact with each other, thereby forming a lamellar phase and an interface between the first composition and second composition; detecting the displacement of the indicator in the organic phase, wherein the displacement of the indicator in the organic phase indicates the presence of the specific analyte; and repeating steps a-e for multiple analytes, wherein a computer system is used to analyze and store data regarding chemical kinetics of each analyte, thereby creating individual profiles for each analyte which can be used in a high throughput assay to detect multiple analytes contemporaneously.

In some aspects, said computer system can employ machine learning. A computer system can include, but is not limited to, a notebook computer, desktop computer, laptop computer, mobile phone, or server. As used herein, machine learning can refer to the process of a computer system learning over time without being explicitly programmed. The machine learning module can apply various machine learning algorithms, techniques, methods, or any combination thereof to the individual profiles for each analyte.

In certain aspects, the indicator and reagents used can be specific for the analyte, so that the indicator is displaced in the presence of the analyte, Product Biosensor for Detection of a Specific Analyte In a further aspect, provided herein is a biosensor for detection of a specific analyte, wherein the biosensor includes an organic droplet inside of an aqueous phase; an indicator dissolved in an organic phase; and a lamellar phase, wherein said aqueous phase includes a test analyte, and further wherein said indicator moves from the organic phase to the aqueous phase in the presence of the specific analyte.

In some aspects, the indicator and reagents used can be specific for the analyte, so that the indicator is displaced in the presence of the analyte.

In certain aspects, said biosensor can be a microfluidic device.

A number of embodiments of the disclosure have been described. Nevertheless, it will be understood that various modifications may be made without departing from the spirit and scope of the invention. Accordingly, other embodiments are within the scope of the following claims.

By way of non-limiting illustration, examples of certain embodiments of the present disclosure are given below.

EXAMPLES

To further illustrate the principles of the present disclosure, the following examples are put forth so as to provide those of ordinary skill in the art with a complete disclosure and description of how the compositions, articles, and methods claimed herein are made and evaluated. They are intended to be purely exemplary of the invention and are not intended to limit the scope of what the inventors regard as their disclosure. These examples are not intended to exclude equivalents and variations of the present invention which are apparent to one skilled in the art. There are numerous variations and combinations of process conditions that can be used to optimize product quality and performance. Only reasonable and routine experimentation will be required to optimize such process conditions.

Example 1: Partitioning Indicator Displacement Assay

Methods

The experimental setup is shown in FIGS. 1A-1D. The organic drops with fully dissolved indicator were exposed to an aqueous phase containing the target analyte. Over time the target analyte displaced the indicator and partitioned into the organic phase. In this experiment, the sensor had various concentrations of CTAB dissolved into the organic phase and used the maximum saturation ratio of blue dye to CTAB (Mechanism paper) to saturate each organic phase solution with the indicator, blue FCF dye. The displacement of blue dye from the organic phase was measured by monitoring optical transmittance using a color camera.

Erioglaucine disodium salt (Blue 1), 1-octanol (112615) and Adenosine 5'-triphosphate disodium salt hydrate (ATP) were purchased from Sigma-Aldrich (St. Louis, MO, USA). Deionized water was used to dissolve both the dye and the ATP. ATP was dissolved in a 1M HEPES buffer calibrated to pH 7.1. The size association experiment used 0.1-10 μL disposable sterile pipet tips (VWR) to place droplets of varying sizes onto microscope slides manufactured by Azer Scientific (Unifrost). A barrier of 0.1 mm thick double-sided tape was used to control the environment and as a spacer between the slide and cover slip (25 mm×25 mm) manufactured by VWR.

Martini force fields (MFF) [ref] were used in the coarse-grained molecular dynamic (CGMD) simulations. All CGMD simulations were performed using LAMMPS open source software. The system has two phases, one was the organic phase, the other was the water phase. Blue dye and CTAB was evenly distributed in the oil phase, and ATP was evenly distributed in the water phase.

Five concentrations (60 mM, 30 mM, 15 mM, 7.5 mM, and 3.75 mM) of CTAB in octanol were placed in a tube along with 50 μM of blue dye dissolved in D.I. water, set on a shaker and allowed to equilibrate. An array was made with a sample of each concentration with the blue dye; with 11 drops (replicates) of each concentration and viewed using a DinoLite microscope. Four-hundred μM of aqueous red dye was flowed into the array and a picture was taken before addition of red dye and then every 5 seconds over a 15 minute period. At 15 minutes, polarizers were crossed, and a micrograph taken, 60 mM showed birefringence. Images were analyzed in imageJ, using 5 points within each replicate and 25 points for background analysis. The replicates were then separated by channel as gray values of the micrographs, and data normalized into absorbance values by subtracting the original dye free data from each replicate. The replicates were averaged per concentration and the data was transferred into percent transmittance using the formula Log (1/absorbance).

Results and Discussion

To study the properties of the partitioning indicator displacement assay (PIDA), Allura red dye was chosen to be the analyte. The optical properties of the Allura red dye also allowed for easier analysis to gain a deeper understanding of how partitioning indicator displacement assay works before moving on to other analytes, such as biological proteins and polymers. FIGS. 2A-2B show the experimental results of detection of Allura red dye using the partitioning indicator displacement assay (PIDA) set-up specified in FIGS. 1A-1D. It can be seen that with lower concentrations of CTAB, such as 3.75 mM and 7.5 mM, the blue dye indicator began to be displaced almost immediately, whereas with higher concentrations of CTAB, such as 15 mM and 30 mM, there was a delay in displacement onset time. Given enough time though, all concentrations of CTAB allowed for the displacement of the blue dye indicator by the red dye analyte.

To further examine and quantify the onset delay times in indicator displacement, rate of displacement, and other kinetic properties of the blue dye indicator and red dye analyte system, Trust Region Reflective (TRF) algorithm was used to fit equations for each CTAB concentration. In FIGS. 3A-3D and FIGS. 4A-4B, the fitting of these equations to each line is shown.

The resulting displacement equations from the fitting matched the previously seen experimental delay in displacement onset time of higher CTAB concentrations. More specifically, 30 mM CTAB drops had a delayed onset time of 7.76 minutes whereas the 3.75 mM CTAB drops had no delay in onset time. Also, from the fittings the rate of displacement was also calculated. The 3.75 mM CTAB drops and the 7.5 mM CTAB drops had the fastest rate of displacement of 0.48 sec-1 and 0.42 sec-1 respectively. The higher the concentration of CTAB, the slower the rate of displacement.

The fitting data suggested that both the decay constant, which is called the displacement rate, and the delay in onset time, are dependent on CTAB concentration (FIGS. 3A-3D and FIGS. 4A-4B). This suggested that the ratio of CTAB to red dye impacted the formation of the multilayer anisotropic phase that formed at the interface between the aqueous and organic phases, thus meaning a certain ratio of red dye to CTAB could initiate the dissociation of the anisotropic multilayer phase and cause the red dye to displace the blue dye from the organic phase. This CTAB to red dye ratio threshold could have resulted in the decay constant decreasing for increasing CTAB to red dye ratios. Similarly, it has been shown that increasing CTAB concentrations increased the thickness of the multilayer phase formed at the interface. This increase in thickness could result in the dyes taking a longer time to partition in and out of the organic phase resulting in a decreased displacement rate. Additionally, the increase in viscosity caused by the increase in CTAB concentration could also have impacted the inverse proportionality of displacement rate and CTAB concentration. Another possibility is that blue dye and CTAB micelles leaked out into the aqueous phase over time.

The main goal of this assay was to detect molecules of biological importance or molecules of interest in a new and unique way. This partitioning indicator displacement assay can be used to detect molecules of biological importance such as DNA. It was observed that at CTAB concentrations of 3.75 mM, 7.5 mM, and 15 mM, the blue dye indicator was displaced by vector DNA. It should also be noted that the concentration of analyte DNA fell below the salt concentration needed to displace the blue dye indicator.

Conclusions

Phase separation can have an integral role in biology, chemistry, engineering, and physics. Phase separation has been used for drug delivery (Blaker et al.), the study of disease (Boeynaems, et al.), and catalysis (Entezari et al.). This experiment introduced a new and innovative way to harness phase separation phenomenon to detect other molecules. PIDAs relied on the displacement of an optical indicator from one phase to another. In this experiment, CTAB dissolved in the organic phase was akin to the receptor and blue dye was the optical indicator. The detection of other biological molecules such as DNA was also shown to be possible using PIDAs.

Example 2: Partitioning Indicator Displacement Assay Using CTAB as a Receptor and Blue Dye as an Optical Indicator

Introduction

Indicator displacement assays work by detecting the replacement of an indicator from a molecular binding site by an analyte. The binding sites are typically on individual molecules, such as proteins, aptamers, or occasionally synthetic molecules capable of carrying out molecular recognition by means of selective binding. Described herein is a new sensing mechanism based on analyte partitioning in a two-phase system where the receptor is one of the phases, referred to as a partitioning indicator displacement assay (PIDA). An indicator that is partitioned into the organic phase along with organic solutes is displaced by an analyte introduced into the aqueous phase. The indicator concentration in the receptor phase can be monitored optically leading to label free detection of analytes. A sensor using CTAB/octanol/blue 1 as the receptor phase was found to be selective for the small molecule, red 40 when compared to other similarly charged analytes. Fits to the sensograms reveal a quantitative trend consistent with a supramolecular layer whose thickness corresponds to organic solute concentrations. Coarse grained molecular dynamics simulations provide insights into the mechanisms behind the supramolecular aggregation that occurs at the interface leading to the selectivity of the assay. The idea that a fluid organic phase could be selective in this way depending on additives provides a new way of thinking about biomolecular recognition from a supramolecular perspective. The assay described here has potential for detection of small molecules and implications for biological signaling in phase separated systems are discussed.

In the recent years, there has been in increase in the development and creation of biosensors utilizing supramolecular-based molecular sensors, otherwise known as indicator displacement assays (IDAs). These IDAs generally consist of a supramolecular assembly which includes an optical indicator that is reversibly bound to a synthetic receptor. In the presence of an analyte, the optical indicator will be displaced from the synthetic receptor resulting in an optical signal. IDAs have proven to have many effective applications in the fields of industrial, agriculture, environmental, and biological sciences. (Zhong, 2021; Sedgwick, 2021; Mitchell, 2021.) Additionally, indicator displacement can be used to detect binding in biochemical assays. However, there are still many limitations that need to be surmounted if the full capability of this technique is to be recognized. Some of these limitations include low signal-to-noise ratio and sensitivity of IDAs (Sedgwick, 2021).

Described herein is a displacement assay where the indicator is displaced from one phase into another. An organic phase is used with the indicator dissolved in it, and analyte is added in a second aqueous phase. The analyte displaces the indicator from the organic phase into the aqueous phase, allowing for analyte detection by monitoring the change indicator concentration within the organic phase. This approach utilizes complex and dynamic supramolecular receptors that may transiently form in the organic phase or at the interface, rather than using single molecules or well-defined supramolecules as the receptor (Bell, 2020). This displacement assay is called a partitioning indicator displacement assay (PIDA). Lipid droplet arrays will be made based on the optimal material. First steps will be taken to apply this technology to large molecules such as DNA. The central goal of this project is to develop a general sensor that could selectively detect molecules by using a combinatorial material. The concept of displacement is utilized in pharmacology, where drug binding proteins in the blood can sequester drugs making them less bioavailable. Understanding displacement helps with understanding drug interactions, as taking a second drug can displace the first drug from drug binding proteins leading to toxicity that would not be observed at the dosage of a single drug (Rowland, 1973). This mechanism also has implications in biological systems, where small molecules may be displaced from nonpolar condensates such as lipid bilayers, lipid droplets, or other phase separated compartments. (Alberti, 2017) Phase separation plays an important role in regulation of enzymatic activity, gene expression, higher order chromatin organization, and the breakdown of misfolded proteins (Zhang, 2020; Peng, 2020; O'Flynn, 2021; Alberti, 2017; Hyman, 2014).

Molecular dynamics (MD) simulations play an important role in explaining and predicting the mechanism behind the displacement phenomenon through a microscopic level. MD simulation is able to track the binding and replacing dynamics of different molecules through non-covalent interactions. Compared with all-atomistic (AA) MD simulations, coarse-grained (CG) MD simulations are advantageous to handle large systems with ~1 million particles and a time scale of 50 microseconds with reasonable demands of computational resources and power. Especially, when the molecules are too big, there is no need to keep track of the trajectory of each atom, CG MD would help group certain atoms in one molecule to be a whole bead, which still maintains the function of the functional group but greatly reduces the size of the whole system.

In a recent study, MD simulations in combination with experimental data was used to investigate possible mechanisms of surfactant-based molecular recognition. In conjunction, both methods supported the hypothesis that a specific concentration of CTAB in an organic phase is able to display selective partitioning between two different dye molecules due to a lamellar phase that forms at high CTAB concentrations. These results suggest that lipid aggregation and phase transitions may have a greater role in determining some physical and biological properties in complex systems.

Experimental Section

Aqueous Phase Preparation

The Allura red AC (Red 40) was obtained from TCI (Tokyo, Japan). Deionized water was used to dissolve the red 40 dye. Adenosine triphosphate (ATP) was dissolved in a 20 mM HEPES buffer calibrated to pH 7.1.

Organic Phase Preparation

The organic solute cetyltrimethylammonium bromide (CTAB) was purchased from Sigma-Aldrich (St. Louis, USA). Erioglaucine disodium salt (Blue 1) was purchased from Sigma-Aldrich (St. Louis, MO, USA). 10 mL of 6 mM, 3 mM, 1.5 mM, 0.75 mM, and 0.375 mM blue 1 dye dissolved in deionized water and added to separate tubes containing 2 mL of different concentrations of CTAB in octanol (60 mM, 30 mM, 15 mM, 7.5 mM, and 3.75 mM), set on a shaker and allowed to equilibrate. After equilibrating for one week, the organic layer of each CTAB concentration containing the blue 1 dye was used to make the microarray.

Assay Microarray and Flow Cell Assembly 50 nL octanol drops containing CTAB and blue 1 dye were placed onto microscope slides manufactured by Azer Scientific (Unifrost) using 0.1-10 µL disposable sterile pipet tips (VWR). A barrier of 0.3 mm PDMS was used as a spacer between the slide and cover slip (25 mm×25 mm) manufactured by VWR. Approximately 135 µL of analyte solution was added to the flow cell and moved quickly through the flow cell.

Optical Characterization

Samples were imaged with a digital microscope (Dino-Lite Pro2 AD-413T or Dino-Lite Edge AM4115ZT) at 100 Å~ magnification. For imaging PIDA assays, a portable backlight stage (Dino-Lite MSBL-ZW1R) was used as a white light source and positioned under the bottom of the slide to illuminate the sample. Images for measurement of the transmittance were captured in brightfield mode. The time dependent partitioning was recorded at one frame per 20 second intervals.

Data Analysis

Images were analyzed in imageJ, using 10 points within each replicate and 25 points for background analysis. The replicates were then separated into different RGB channels as gray values of the micrographs. The data was then normalized into transmittance values by subtracting the original dye free data from each replicate. The data was then converted into absorbance using the formula Log (2−transmittance). Using the absorbance data, and the measured initial blue dye concentrations, the data was converted to blue dye concentration and then the replicates were averaged per concentration and the standard deviation was calculated. Graphs showing the separate channels of the micrographs, with the red color (b) or blue color (e) that was viewable with the DinoLite, and how they differed with concentration (B and E). The graphs are made from each of the 5 concentrations with their associated normalized absorbance values. Pixel intensities were extracted using image processing software, ImageJ (downloaded from the NIH website, http://imagej.nih.gov/ij/). Analysis was automated using a script written for the statistical computation program "R". The software used coordinates extracted from the image processing program (ImageJ) and created a macro line item for circles of diameter 6 pixels (unless otherwise noted) centered at the coordinates given. The "R" script then acquired the pixel values from the red and blue channels and used them to calculate absorbance and selectivity values.

Fitting Methods

Absorbance along with time curve was fitted under exponential function $y=\exp(-a*(x+b))$, where a is rate of displacement and b is the onset delay time. An exponential regression function with trust region reflective (trf) algorithm was used to optimize the experimental data. After the rate of displacement of onset delay time was obtained, linear fitting was used to study the relationship.

Computational Methods

Martini force fields (MFF) will be used in the CGMD simulations. All CG MD simulations are performed using LAMMPS open-source software. The system has two phases, one is the organic phase, the other is the water phase. Blue dye and CTAB are evenly distributed in the oil phase, and ATP is evenly distributed in the water phase.

Results and Discussion

The experimental setup is shown in FIG. 1. Utilizing the same microfluidic device set-up from the Bell et al. (2020) study, the organic drops with indicator fully dissolved in are exposed to an aqueous phase containing the target analyte. Over time the target analyte will displace the indicator and partition into the organic phase. In this experiment, the sensor has various concentrations of CTAB dissolved into the organic phase and uses the maximum saturation ratio of blue dye to CTAB (1:2) to saturate each organic phase solution with the indicator, blue FCF dye. (National Center for Biotechnology Information, PubChem Compound Summary for CID 19700, Brilliant Blue FCF, 2020.) The displacement of blue dye from the organic phase is measured by monitoring optical transmittance using a color camera.

To study the properties of the partitioning indicator displacement assay (PIDA), Allura red dye was chosen to be the analyte. (National Center for Biotechnology Information. PubChem Compound Summary for CID 33259, Allura Red AC Dye, 2020.) The optical properties of the Allura red dye also allow for easier analysis to gain a deeper understanding of how partitioning indicator displacement assay works before moving on to more complex analytes, such as biological proteins and polymers. FIG. 2 shows the experimental results of detection of Allura red dye using the partitioning indicator displacement assay (PIDA) set-up specified in FIG. 1. It can be seen that with lower concentrations of CTAB, such as 3.75 mM and 7.5 mM, the blue dye indicator begins to be displaced immediately after coming in contact with the analyte solution whereas with higher concentrations of CTAB, such as 15 mM and 30 mM, there is a delay in displacement onset time. Given enough time though, all concentrations of CTAB that are soluble in octanol allow for the displacement of the blue dye indicator by the red dye analyte.

A good biosensor needs to be fast, reliable and repeatable while being highly specific to the analyte. To demonstrate that a PIDA has all of these qualities, the limit of detection was characterized with decreasing CTAB concentration and drop size. Additionally, different analytes were used to examine the specificity of the PIDA.

Previous experiments using a CTAB containing octanol drops and a mix of blue and red dye showed a CTAB concentration dependent switch (Bell, 2020). Specifically, low concentrations of CTAB (7.5 mM and lower) drops were selective for red dye. It was also noted higher concentrations of CTAB were initially selective for blue 1 dye and would switch after a period of time to be selective for red 40 dye. Therefore, it was proposed to determine the limit of detection in relation to CTAB concentration (FIG. 3a). The limit of detection is typically defined as the lowest concentration that can be measured with statistical significance by means of a given analytical procedure. Additionally, LOD in this PIDA is dependent on the specified time period that the assay is allowed to proceed. Therefore, an increased rate of displacement within a specified period of time would result in an increased amount of indicator displacement and consequently a lower limit of detection. For this experiment, PIDA run time was set to 10 minutes. The limit of detection was shown to decrease with decreasing CTAB concentration. It can also be hypothesized that even lower CTAB concentrations would result in lower limits of detection.

Additionally, the switch in dye selectivity from the Bell et al. study was shown to occur faster at smaller drop sizes and to take longer with increased drop size, therefore it is probable that rate of the displacement is also proportional to drop size. Future studies aim to improve this limit of detection by comparing the amount of indicator displacement of different drop sizes.

Figure 7A:
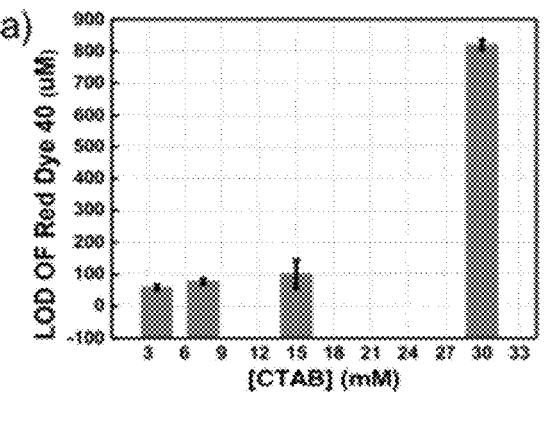
FIGS. 7A-7B show limit of detection and selectivity of portioning indicator displacement assay (PIDA). a) Limit of detection of PIDA sensor for different concentrations of CTAB containing octanol drops. Graph shows limit of detection for the analyte red 40 dye ten minutes after the addition of analyte. The limit of detection for this sensor is defined as the lowest analyte concentration that displaces 5% of the blue 1 FCF dye indicator from the organic phase. b) Specificity of Partitioning Indicator Displacement Assay (PIDA) using 7.5 mM CTAB containing octanol drops and blue 1 FCF dye indicator. Graph shows concentration of blue 1 FCF dye remaining in CTAB containing organic drops 10 minutes after the addition of analyte flow for six different analytes.
Figure 7B:
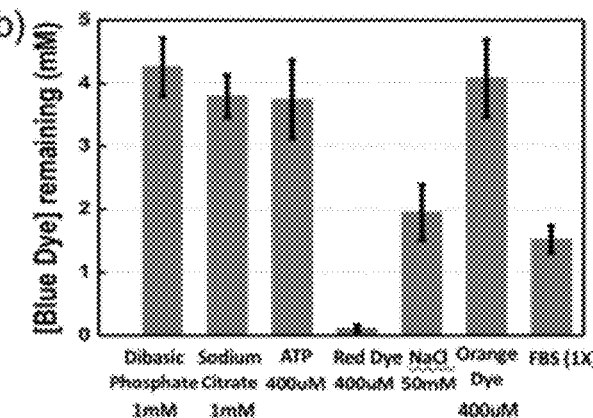

A goal of this assay is to detect molecules of biological importance or molecules of interest in a new and unique way. First this PIDA with blue dye as an indicator was used to try to detect small negatively charged molecules like adenosine triphosphate (ATP) and citric acid. However, it was found that this assay is unable to detect those molecules. This demonstrates that the PIDA using the CTAB-blue 1 dye system is specific for certain analytes, such as Allura red 40 dye (FIG. 7B). Additionally, 50 mM sodium chloride was shown to approximately displace 48.3% of the blue dye indicator after 10 minutes demonstrating the PIDA's ability to detect analytes dissolved in salt solutions. Furthermore, the analytes with a seemingly higher concentration of blue dye remaining than the initial blue dye concentration can be attributed to error between replicates. This error is accounted for in the error bars. Additionally, for the analytes dibasic phosphate and sodium citrate some error can be attributed to changes in path length as the drops compress over time and error caused by the limited detection range of the camera.

Figures 12, 13, 14A, 14B, 14C, 14D, 14E:
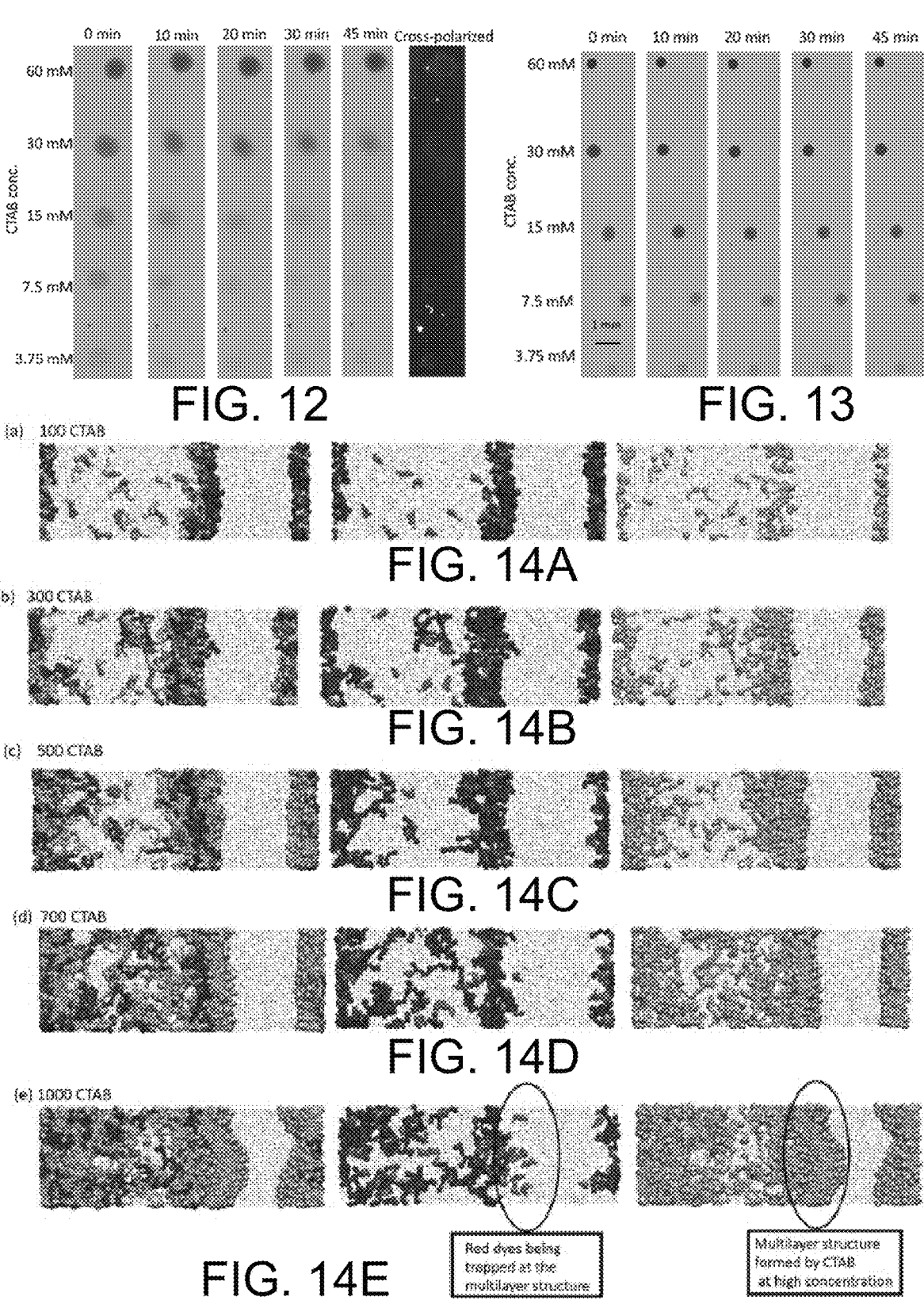
FIG. 12 shows images showing blue dye displacement by 585.2 ng/uL Vector DNA at different CTAB concentrations over time.
FIG. 13 shows images showing no blue dye displacement by negative control for Sup.
FIGS. 14A-14E show MD simulations are consistent with experimental results. When CTAB concentration is low as (a), red dye displaces blue dye. When CTAB concentration is high as (e), red dye molecules are trapped at the interface which has a clear lamellar phase, which prevents the blue dye from being displaced.

After this larger negatively charged polymers, such as DNA were used as an analyte in this assay. FIG. 12 shows how this partitioning indicator displacement assay can be used to detect molecules of biological importance such as DNA. It was observed that at CTAB concentrations of 3.75 mM, 7.5 mM, and 15 mM, the blue dye indicator was displaced by vector DNA. It should also be noted that the concentration of analyte DNA falls below the salt concentration needed to displace the blue dye indicator. Analytes with similar charge and structure such as RNA and ssDNA are also likely to be able to be detected using this PIDA system.

Figure 8:
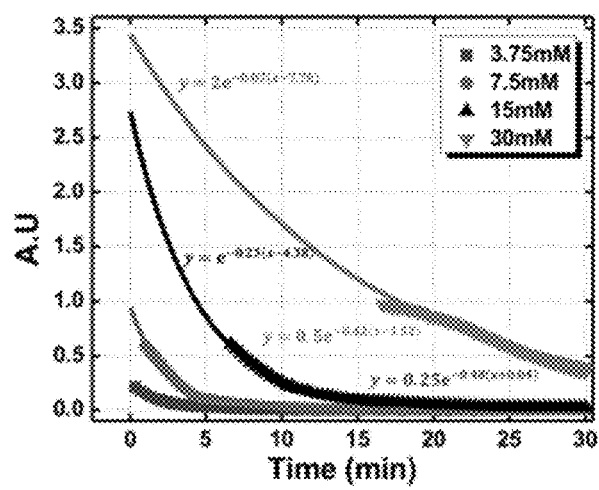
FIG. 8 shows displacement fitting of different concentrations of CTAB. Calculated displacement equations for different concentrations used in the PIDA with a blue 1 dye indicator and a red 40 dye analyte. Displacement equation fittings for 3.75 mM, 15 mM, 7.5 mM, and 30 mM are shown.
Figure 9A:
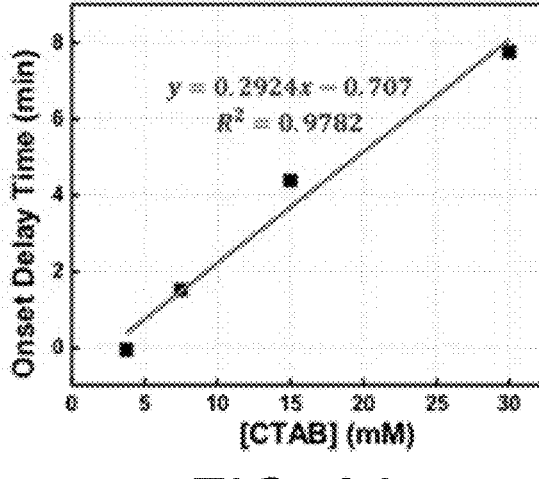
FIGS. 9A-9B shows delay in onset of displacement and displacement rate is proportional to CTAB concentration. a) Graph showing onset delay time versus CTAB concentration. b) Graph showing rate of displacement versus CTAB concentration.
Figure 9B:
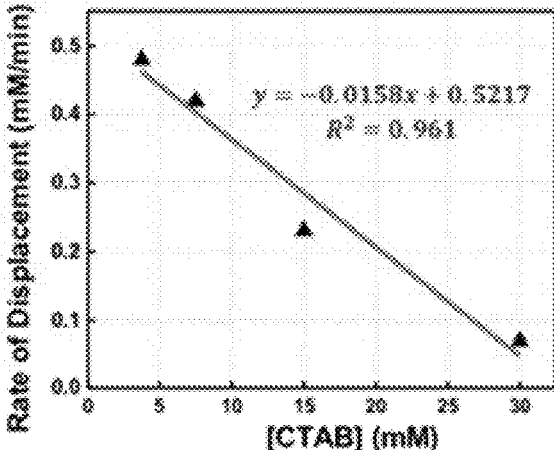

To further examine and quantify the onset delay times in indicator displacement, rate of displacement, and other kinetic properties of the blue dye indicator and red dye analyte system, Trust Region Reflective (TRF) algorithm was used to fit equations for e ach CTAB concentration. In FIG. 8, the fitting of these equations to each line is shown.

The resulting displacement equations from the fitting match the previously seen experimental delay in displacement onset time of higher CTAB concentrations. More specifically, 30 mM CTAB drops had a delayed onset time of 7.76 minutes whereas the 3.75 mM CTAB drops had no delay in onset time. Also, from the fittings the rate of displacement was also examined using the decay constant. The 3.75 mM CTAB drops and the 7.5 mM CTAB drops had the fastest rate of displacement of 0.48 sec-1 and 0.42 sec-1 respectively. The higher the concentration of CTAB the slower the rate of displacement; for example, 30 mM CTAB had a displacement rate of 0.07 $sec^{-1}$.

The fitting data seems to suggest that both the decay constant (b), referred to as the displacement rate, and the delay in onset time (c) are dependent on CTAB concentration (FIG. 8). This could indicate that the ratio of CTAB to red dye is important for the formation of the multilayer anisotropic phase that forms at the interface between the aqueous and organic phases meaning there could be a certain ratio of red dye to CTAB needed to initiate the dissociation of the anisotropic multilayer phase and let red dye displace the blue dye from the organic phase. This CTAB to red dye ratio threshold could result in the decay constant decreasing for increasing CTAB to red dye ratios. Similarly, it has been shown that increasing CTAB concentrations increases the thickness of the multilayer phase formed at the interface (ref Mechanism manuscript). This increase in thickness could result in the dyes taking a longer time to partition in and out of the organic phase resulting in a decreased displacement rate. Additionally, the increase in viscosity caused by the increase in CTAB concentration could also be a reason for the inverse proportionality of displacement rate and CTAB concentration. Another possibility is that blue dye and CTAB interact to form micelles that leak out into the aqueous phase over time. (Ueda, A. C.; de Oliveira, L. H.; Hioka, N.; Aznar, M. Liquid-Liquid Extraction of Basic Yellow 28, Basic Blue 41, and Basic Red 46 Dyes from Aqueous Solutions with Reverse Micelles. J. Chem. Eng. Data 2011, 56, 652-657, DOI: 10.1021/je1008558.)

Previous studies have indicated that the mechanism for surfactant based molecular recognition is dependent on surfactant concentration in the organic layer and the ability of the surfactant to create an anisotropic phase which segregates the two dyes. (Bell 2020; Fontell, K.; Khan, A.; Lindstrom, B.; Maciejewska, D.; Puang-Ngern, S. Phase-Equilibria and Structures in Ternary-Systems of a Cationic Surfactant (C16tabr or (C16ta)2so4), Alcohol, and Water. Colloid Polym. Sci. 1991, 269, 727-742, DOI: 10.1007/bf00657411.) More specifically, at equilibrium, the red dye was shown to be more thermodynamically favorable to partition into the organic phase than the blue dye. Yet, before equilibrium was reached at high CTAB concentration the blue dye would partition in first before later being displaced by the red dye. A 2022 study showed that at high CTAB concentration, a multilayer phase composed of CTAB would trap the red dye at the octanol-water interface, allowing the blue dye to partition into the organic phase before the red dye. And at low CTAB there would be no multilayer formation allowing the red dye to partition into the octanol layer. This example used a combination of MD simulations and experiments to further elucidate this mechanism in the context of indicator displacement.

Coarse grained molecular dynamics simulations provide insights into the mechanism of the displacement and selectivity of the assay, as shown in FIGS. 10A-10E and 11. In a separate study, a coarse-grained molecular dynamics model was developed to understand the selectivity mechanisms of partitioning experiments where both blue and red dye are initially in the water before diffusing into the organic phase. (Bell, 2020.) (H. Zhou, E. Shiel, T. Bell, S. Lin, S. Lenhert, Mechanism of Surfactant-Based Molecular Recognition.) The model was found qualitatively consistent with several trends observed in those experiments. Here the initial structure of the simulation begins with CTAB and the blue dye in the octanol phase, and the red dye in the aqueous phase (FIG. 11*a*) as is the case in the indicator displacement experiments. At low CTAB concentrations, the blue dye is displaced from the organic phase and replaced by the red dye is also carried out, and as in the experiments the blue dye remains in the octanol phase, oris incompletely displaced. FIG. 7 shows quantification indicating that as the CTAB concentration increases, less displacement is observed, and a higher amount of red dye accumulates at the interface. Note that in experiments the dye at the interface isn't visible due to low amounts of dye there, although the simulation allows visualization of these molecules.

Figures 10A, 10B, 10C, 10D, 10E, 11A, 11B, 11C, 11D:
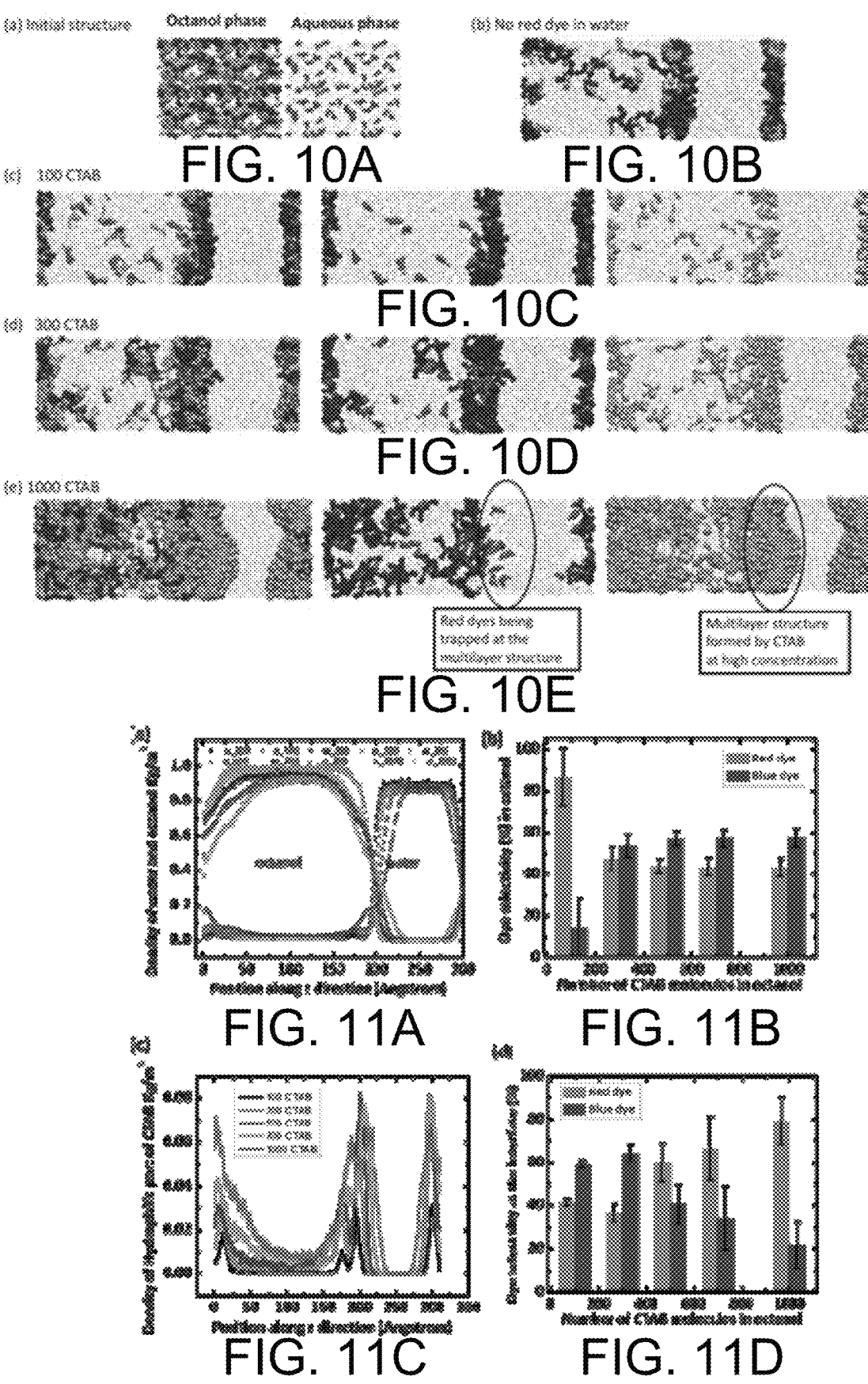
FIGS. 10A-10E shows MD simulations are consistent with experimental results. (a) and (b) show the initial structure of the MD simulation before the addition of red dye. When CTAB concentration is low as (c), red dye displaces blue dye. When CTAB concentration is high as (e), red dye molecules are trapped at the interface which has a clear lamellar phase, which prevents the blue dye from being displaced.
FIGS. 11A-11D shows comparison of both dye concentrations in octanol phase (b) and at the interface (d). In (c), it is clear that the lamellar phase formed by high CTAB concentration at the interface.

As in the experiments shown here, the amount of CTAB in the simulation is varied (FIG. 10C-10E).

At low CTAB concentrations, the blue dye is seen to be quickly displaced from the organic phase and replaced by the red dye. However, at higher CTAB concentrations, a lamellar phase forms and the blue dye is incompletely displaced. (Fontell, K.; Khan, A.; Lindström, B.; Maciejewska, D.; Puang-Ngern, S. Phase-Equilibria and Structures in Ternary-Systems of a Cationic Surfactant (C16tabr or (C16ta)2so4), Alcohol, and Water. Colloid Polym. Sci. 1991, 269, 727-742, DOI: 10.1007/bf00657411.) Such a lamellar phase was also observed in the study for selective partitioning without displacement. The red dye can be seen to accumulate in this lamellar phase, as highlighted in FIG. 10*e*, while the blue dye does not. This suggests a possible mechanism for the delayed displacement observed in experiments at higher CTAB concentration, as the red dye may take longer to cross the lamellar phase the thicker it is.

FIGS. 11A-11D shows quantification of the simulation data. FIG. 11*a* shows identification of the two phases, and then counting of the percentage of red or blue dye molecules in the octanol phase. At low CTAB concentration red dye can be seen to clearly displace the blue dye, but less so at higher CTAB concentration. This is understandable as higher CTAB concentration allows more binding sites for both dyes to be present. FIG. 11C shows the density profiles of the hydrophilic part (the amino group) on CTAB in order to see molecular distribution and ordering near the interface. At higher CTAB concentrations, multiple peaks become apparent indicating the lamellar phase. Counting of the dye molecules at the interface in FIG. 11*d* shows increasing red dye at the interfacial layer as the thickness of lamellar phase increases. The results of the simulation suggest that the higher affinity of the red dye for the CTAB explains the displacement, while the supramolecular structure at this lamellar phase can explain the CTAB dependent kinetics.

Example 3: Mechanism of Surfactant-Based Molecular Recognition

Introduction

Lipids play a vital role in the molecular organization of all cellular life. There is evidence that aggregates of lipids and lipid-like molecules are capable of selectively binding or regulating the partitioning of other molecules. A model two phase octanol/water system can demonstrate selective partitioning of red 40 and blue 1 dye added to an aqueous phase, with the selectivity depending on surfactants (e.g., CTAB) dissolved in the organic phase. The mechanism of molecular recognition in this system is demonstrated using quantitative partitioning experiments and molecular dynamics simulations. Results indicate that the selectivity for the red dye is thermodynamically favored at all surfactant concentrations, while selectivity for the blue dye is kinetically favored at high surfactant concentrations. The kinetic selectivity for the blue dye correlates to the presence of molecular aggregation at the oil-water interface. Coarse grained molecular dynamics simulations elucidate nanoscale supramolecular structures that can preferentially bind one small molecule rather than another at an interface, providing a selectively permeable barrier in the absence of protein. The results suggest a new supramolecular aptamer-based mechanism for molecular recognition that should be considered in biological systems.

Molecular recognition is perhaps the most fundamental function of biological macromolecules. The ability for a biological molecule to selectively bind to other molecules is based on non-covalent interactions between a macromolecular binding site and the molecule that is to be bound, such as DNA-protein, (Yan, 2012; Vazquez, 2003) receptor-ligands, etc. (Bender, 1997; Zhou, 2012) Lipids are generally not considered carriers of biological information. However, when one considers lipid aggregates such as micelles, bilayers or other supramolecular structures, the presence of more than one lipid species in various concentrations leads to an information density comparable to that of protein or nucleic acids. (Bel, 2020.) From a biotechnological perspective, such specific interactions contribute to the ability of a drug to trigger specific biological responses while avoiding side-effects due to non-specific interactions. (Klein, 2020.) Understanding biomolecular recognition therefore has various applications in drug discovery and development, (Yan, 2012) drug delivery (Hilt, 2004), biosensing (Yang, 2018), and chemical processing in general. Considered herein is a supramolecular structure as a receptor. In that case, lipids can also carry out biological functions based on lipid combinations that result in specific supramolecular structure.

A model system for the study of surfactant mediated molecular recognition based on the partitioning of dyes in a two-phase system was developed. (Bell, 2020.) These experiments can begin with a mixture of two water soluble dyes dissolved in water, and organic surfactants such as cetyltrimethylammonium bromide (CTAB) dissolved in octanol. CTAB has been used as a phase transfer catalysis by mediating the transfer of ions between phases. (Senthamizh, 2012; Makosza, 2012; Makosza, 2012; Godha, 2019.) The CTAB-mediated transfer of the dyes from the water to the octanol phase can then be monitored optically. The system can demonstrate selectivity for one dye or the other depending on the CTAB concentration in the organic phase. When the CTAB concentration is low, only red dye partitions to the organic phase. When the CTAB concentration is high, the blue dye was found to preferentially partition into the organic phase. Interestingly, at intermediate CTAB concentrations, the blue dye was found to preferentially partition into the organic phase first, but after some time was replaced by the red dye. It was further demonstrated that changes in relative concentration of other surfactants added to the organic phase from a small chemical library can modulate the selectivity. This combinatorial formulation is referred to as a supramolecular aptamer as an analogy to nucleic acid aptamers. (Szostak, 1990.) One possible mechanism behind that surfactant based molecular recognition is that CTAB at high concentrations may form a supramolecular structure that thermodynamically favors partitioning of the blue dye over the red dye as the lowest free energy state. For example, CTAB micelles may form at higher CTAB concentrations which may preferentially bind the blue dye as a thermodynamic minimum. Alternatively, the selective partitioning could be explained as a CTAB dependent difference in kinetics of the dye transfer across the phase boundary. Such a kinetic mechanism could be explained by a supramolecular structure that may form at the water-octanol interface at a high CTAB concentration. Such a layer might form a selectively permeable barrier at the interface that could allow the blue dye to transfer across the interface faster. Another possibility could be related to changes of electrochemical potential involved at the interface when ions transfer. Quantitative partitioning experiments were performed to understand the mechanisms behind the surfactant mediated selective dye partitioning. Determining a structure-function relationship for supramolecular lipid structures experimentally is challenging due to the fact that these supramolecular lipid structures cannot be purified and characterized like typical covalent biological polymers. Thus, molecular dynamics (MD) simulations were used to provide structural insights into the selectivity mechanism.

MD simulations are helpful in explaining experimental phenomena at a molecular level and have been applied in studying the molecular recognition of small molecules and biomolecules in biological systems. These include studies of receptor-ligand interactions,[17, 18] protein-protein interactions, (Rakers, 2015; Reynwar, 2008; Chavent, 2016) and lipid-small molecule interactions for drug delivery interactions. (Pluhackova, 2016; Zhuang, 2016.) In addition, MD simulations have been used to understand mechanisms of ion transfer across an oil-water interface, including applications of surfactants in phase transfer catalysis. (Kikkawa, 2012; Melville, 2005; Oberbrodhage, 2000.) A challenge lies in simulating larger systems which can become computationally intense. Even with the rapid growth and development of supercomputers, all-atomistic MD simulations are still facing the obstacles of higher computational costs and time consuming for larger systems. (Jang, 2016.) Compared with all-atomistic MD simulations, coarse grained (CG) MD simulations for studying biological systems appear to have more advantages, such as saving computational time and resources, as well as handling large time and length scale MD simulations. CG-MD simulations use CG models to simplify the molecular structures by grouping several atoms into CG beads without losing the characteristics of the molecules. Martini force fields (Cesar, 2009; Siewert, 2007) have been developed and parameterized in a systematic way for these CG models and widely used to study the biomolecular systems. Previous works have applied CG models using Martini force fields to study the molecular recognition between small molecules and carbon nanotube polymers (Lin, 2014), DNA (Uusitalo, 2015), RNA (Uusitalo, 2017), and proteins (Monticelli, 2008). In addition, CG-MD simulations have become an increasingly helpful tool for studying small molecules partitioning between organic phase and aqueous phase. (Alessandri, 2021.) CG-MD simulations can also provide microscopic insights about nanostructure-function relationship behind the selectivity, and design as well as engineer new compositions of lipid mixtures that can extract small molecules more efficiently. This is significantly helpful in biological fields.

Results and Discussion

CTAB Dependent Selective Partitioning

Herein, detecting selective partitioning into droplets in a microfluidic device was scaled up to millimeter volumes in tubes, as shown in FIGS. 15A-15B and FIGS. 16A-16B. The selective partitioning behavior of the two dyes between the octanol and water phases was studied in test tubes (FIGS. 15A-15B), and dye concentrations quantified optically. First, solutions of CTAB in octanol and both dyes in water were prepared separately. Then both the aqueous and organic solutions were combined into one tube. After some time, one or both dyes partitioned into the organic phase. Consistent with previous observations, red dye selectively partitioned into the octanol phase at CTAB concentrations (0.5 mM and 1 mM), and the blue dye selectively partitioned into the octanol phase at high CTAB concentrations (30 mM and 60 mM). Due to the larger scale of the experiment, it took between 4-48 hours to observe the selectivity, as compared to 1-10 minutes in the microfluidic setup. (Bell, 2020.) A question about the mechanism of this surfactant mediated molecular recognition was then whether one dye is thermodynamically favored to partition into the octanol in the presence of CTAB or whether it is kinetically driven. For example, it is possible that the blue dye is more thermodynamically favored than the red dye at high CTAB concentration due to the formation of micelles in the organic phase or some other CTAB-mediated aggregation phase at the interface. Another possibility is that the red dye is more thermodynamically favored than the blue dye at all CTAB concentrations due to the stronger electrostatic interactions between red dye and CTAB than blue dye; however, the formation CTAB aggregation at the interface may have created a selectively permeable physical barrier which allows the blue dye to cross the interface more quickly than the red dye. At intermediate CTAB concentrations (e.g., in this geometry, 1 mM CTAB) both dyes initially partition into the octanol together after 4-24 hours, and then after 48 hours the octanol phase can be observed to turn red. In the smaller microfluidic system, this temporal switch in selectivity was observed at higher CTAB concentration (15 mM), suggesting that kinetics may play a role in the selectivity mechanism. To determine which dye, the red dye or the blue dye, is thermodynamically favored at high CTAB concentration, equilibrium state of this system was investigated.

Equilibrium Results

Figures 16A, 16B:
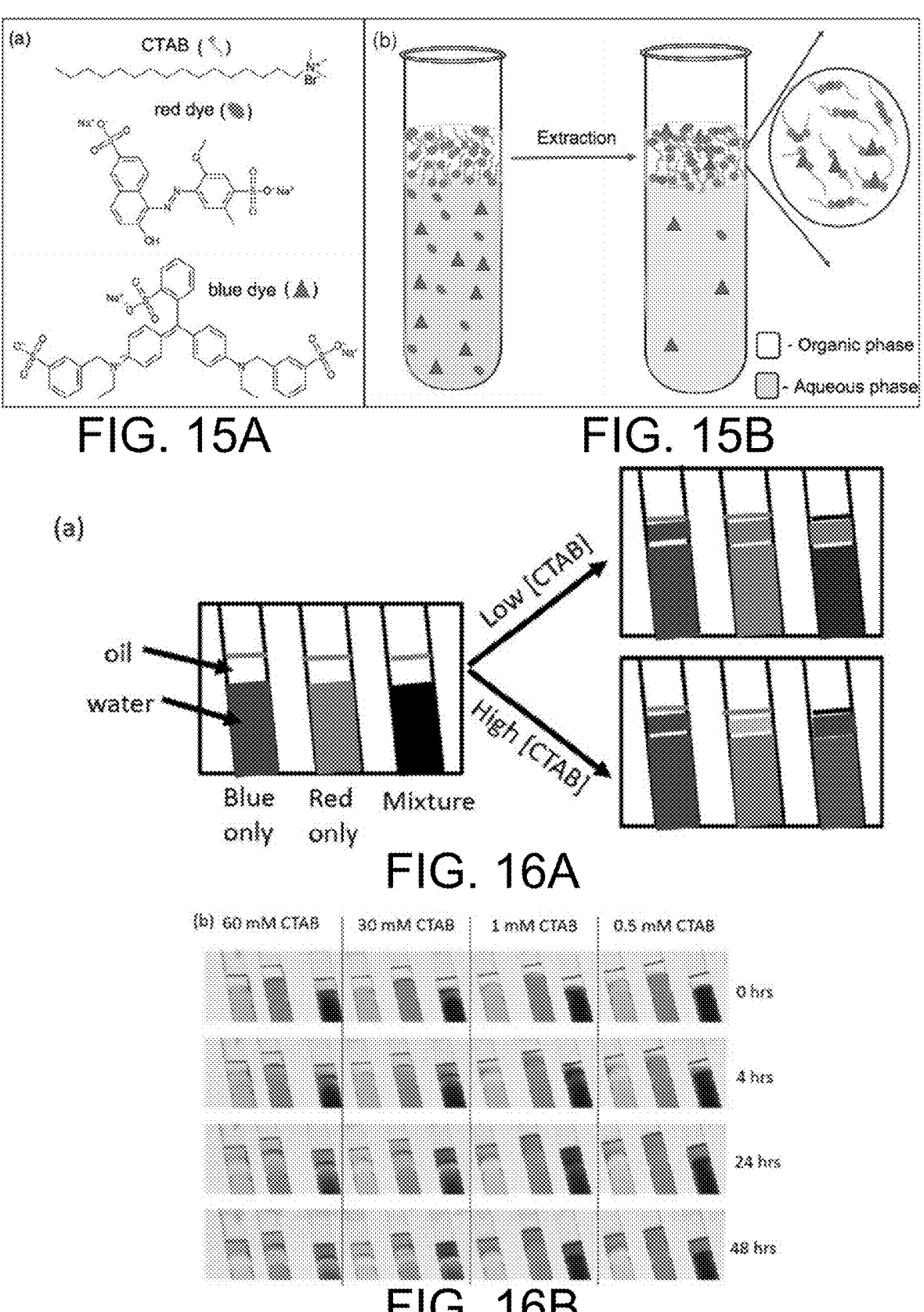
FIGS. 16A-16B shows a schematic and example of the surfactant mediated selective partitioning studied herein. Schematic of experimental setup (a) of tubes in sets of three, pure red dye, pure blue dye, and a mixture of red and blue dye. (b) Experimental tube results of each set with different CTAB concentrations. Partitioning selectivity between red and blue dye at high CTAB concentrations blue dye is more selective for the organic phase and at low CTAB concentrations red dye is more selective.
Figures 17A, 17B, 17C, 18A, 18B, 18C, 18D, 18E:
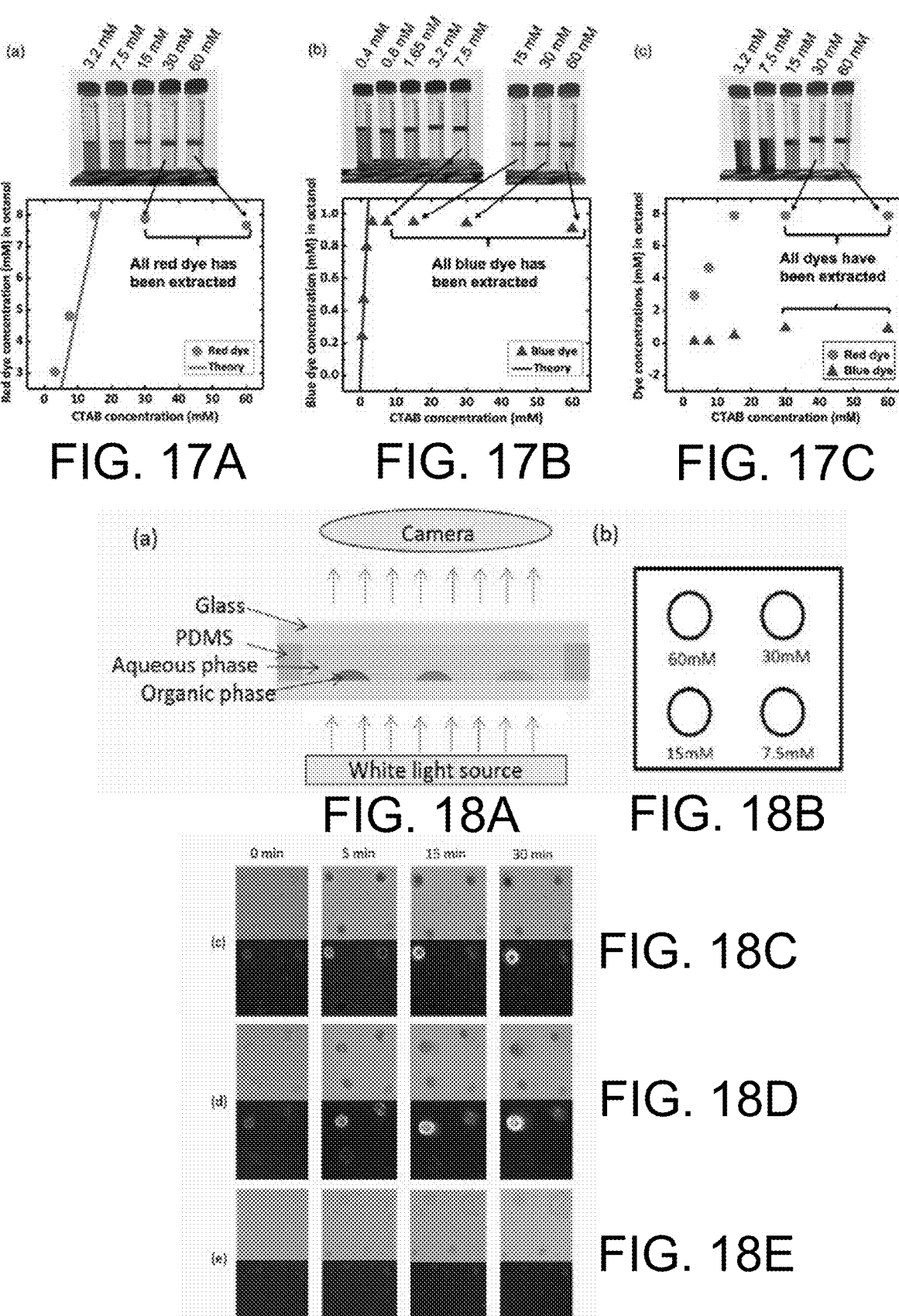
FIGS. 17A-17C shows equilibrated samples showing selectivity for red dye partitioning into octanol at all concentrations, with a ratio of two CTAB molecules per dye. (a) (b) (c) are pure red, pure blue and mixture, respectively. The results indicate that the selectivity for blue observed in non-equilibrated samples is a kinetic effect.
FIGS. 18A-18E shows the correlation of the birefringent ring to selectivity. a) Microfluidic device containing adherent organic droplets exposed to aqueous dye solutions while optical transmittance is monitored using a color camera. b) Set-up detailing the CTAB concentration of drops in (c) (d) and (e). (c) Images of octanol droplets with a mixture of 400 uM Allura Red and 50 uM Blue Dye, (d) only 400 uM Allura Red Dye, and (e) only 50 uM Blue Dye, respectively, using different CTAB concentrations including 7.5 mM, 15 mM, 30 mM, and 60 mM taken at different times. Top image is taken using brightfield and the bottom image is taken using cross-polarized microscopy for (c) (d) and (e). Pure blue doesn't cause a ring, but pure red causes a ring when the CTAB concentration is 30 mM or higher.

To examine the dye partitioning at equilibrium, the two-phase system at various CTAB concentrations, samples were left on a shaker for one week followed by centrifugation and optical characterization of the aqueous phase by absorbance spectroscopy (FIGS. 16A-16B). Tubes containing only the red dye and only blue dye were included in the experiment as well as tubes with the dye mixture. The resulting tubes at equilibrium showed that at high CTAB concentration, all the dye was extracted into the organic phase, while at low CTAB concentration (<15 mM) only red dye partitioned into the octanol phase (FIGS. 17A-17C). Stoichiometric ratios calculated from the amount of each dye left in the water after extraction at the concentrations where not all of the dye was extracted show that for both the red and blue dyes a ratio of approximately 2 CTAB molecules are needed to extract each dye molecule. This stoichiometric ratio result suggests that the maximum saturation ratio for CTAB to dye molecules is dependent on the balancing of charges between molecules. CTAB has a net charge of +1 whereas both dye molecules have a net charge of −2. Thus, two positively charged CTAB can effectively balance the negative charge of the dye molecules resulting in a zero net charge for a complex of two CTAB and one dye molecule. However, these experiments do not reveal which dye is more favorable in the organic phase at high CTAB concentrations due to the CTAB to dye ratio being high enough to accommodate both dyes fully partitioning into the organic phase.

In order to further study the equilibrium state at high CTAB concentrations, the setup was used to allow for observation of the equilibrated state at high CTAB concentrations with excess dye in the water. Using the previously calculated dye ratios needed for maximum saturation in the organic phase, the dye concentrations were chosen so that it would be impossible for both red and blue dye to fully partition into the organic phase. Tubes with a range of concentration from 3.75 mM to 60 mM CTAB dissolved in octanol and deionized water with blue and red dye concentrations ranging from 106 µM to 1700 µM. By observing which dye is left in the aqueous phase after equilibrium is reached, it can be determined which dye is more thermodynamically favorable in the organic phase at equilibrium. If the mechanism for the blue dye selectivity at high CTAB concentrations is thermodynamic in nature and depends on the formation of micelles in the organic phase, then at high CTAB concentrations the dye remaining in the aqueous phase should be the red dye and at low CTAB concentrations, the dye remaining in the aqueous phase should be the blue dye. However, if the mechanism is kinetic and relies on the formation of an aggregation phase at the interface of the two phases, then at all concentrations of CTAB the dye remaining in the aqueous phase should be the blue dye. The result of this experiment was that the red dye was found to preferentially partition into the organic phase at equilibrium at all concentrations tested, leaving the blue dye in the aqueous phase at equilibrium. From this it was concluded that the red dye is thermodynamically favored to partition into the CTAB containing organic phase. These results suggest that the selective partitioning of the blue dye into the organic phase at higher CTAB concentrations is a kinetic effect.

Correlation of Birefringent Ring to Selective Partitioning of the Blue Dye

Since the two-dye tube system equilibrium results indicate that it was likely a kinetic mechanism behind the blue dye selectivity at high CTAB concentrations, cross-polarized microscopy was used to determine if and when an anisotropic phase forms between the two phases using systems of red dye, blue dye, and a mixture of the red and blue dye. The blue and red dye system and the red dye only system both show the formation of an anisotropic structure around the circumference of the 60 mM CTAB drops. Also, it can be observed that there is formation of an anisotropic phase in the 30 mM CTAB drops in the red and blue dye and the red dye only systems before the red dye fully partitions into the organic phase of the drop around 5 minutes. After 5 minutes, as the red dye continues to partition into the organic phase, this anisotropic phase seems to disappear. This can be observed by observing the absence of the anisotropic phase at 10 minutes and all later times for the 30 mM CTAB drops in the red and blue dye and the red dye only systems. Additionally, it was observed that in the absence of red dye, or in the blue dye only system, there is no anisotropic phase formation. This pattern of anisotropic phase formation before the red dye partitions supports the kinetic barrier mechanism which depends on the formation of some anisotropic phase on the interface of the drops with high CTAB concentration that hinders the red dye from partitioning in and allows the blue dye to partition in at a faster rate resulting in the observed high CTAB concentration blue dye selectivity and the low CTAB concentration red dye selectivity in the Bell, 2020 study.

It also should be noted that the temporal switch phenomenon that was observed in the Bell, 2020 study appears to occur at 30 mM CTAB in this study. This can be explained by changes in flow, flow rate, and variation in drop size. As the mechanism for dye selectivity is most likely dependent on a kinetic mechanism, any changes to the kinetics of the system will impact the selectivity results.

Coarse-Grained MD Setup

The coarse-grained (CG) molecular models using Martini force fields are shown in FIGS. 19A-19E. Established CG models for CTAB, octanol, and water are FIGS. 19A, 19B, and 19C, respectively. A molar percentage of 10% of the water molecules was set as antifreeze particles BP4 type. Electrostatic interactions were applied to the system. The dielectric constant was 15.

Figures 19A, 19B, 19C, 19D, 19E, 20A, 20B, 20C, 20D:
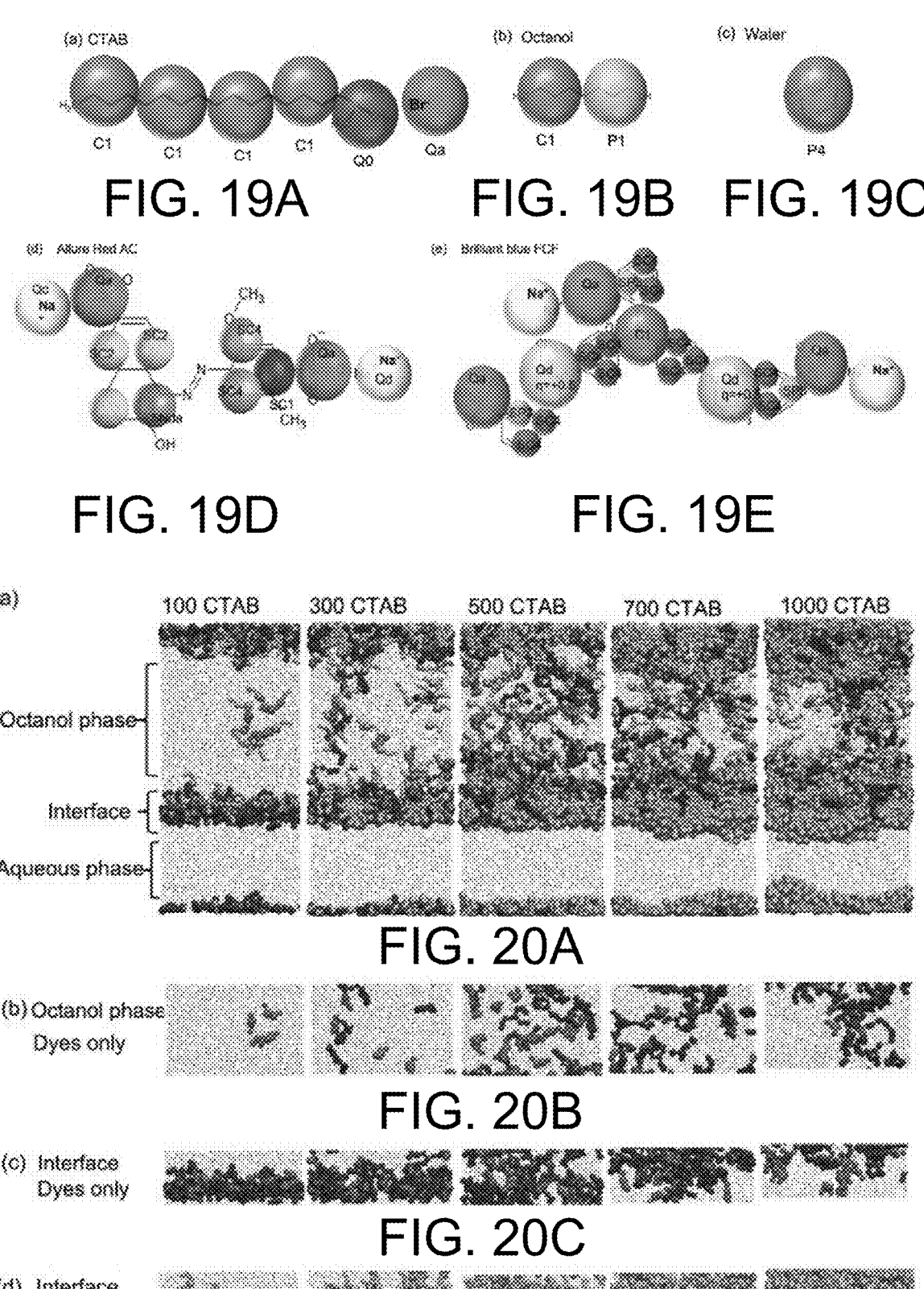
FIGS. 19A-19E shows coarse-grained models for all chemical involved in the experiments using Martini Force Fields 2.0. (Siewert, 2007.)
FIGS. 20A-20D shows a mechanism of the selective switch along with CTAB concentration from low to high. A system contains 10000 CG water molecules (yellow beads), 10000 CG octanol molecules (orange beads), 60 CG red dye molecules (red beads), 60 CG blue dye molecules (blue beads) and 100 CG 300 CG 500 CG 700 CG 1000 CTAB molecules (cyan beads represent the hydrophilic part, green beads represent the hydrophobic part). The figure shows the first images showing all chemicals, the second one only showing CTAB, and third one only showing both dyes in water and octanol.

For red 40 shown in FIG. 19D, the CG model from a similar chemical structure of a voltage-sensitive dye Di-4-ASPBS that has been previously studied was adopted (Hinner). For the blue 1 structure shown in FIG. 19E, it was treated as having a resonance structure (Resonance, 2006), which means there is an election delocalized between two nitrogen atoms resulting in a net charge of +1 for those two groups. This demonstrates that for the coarse-grained model of blue dye in FIG. 19E, both coarse-grained beads that contain nitrogen have a positive 0.5 charge, instead of one CG nitrogen bead has +1 charge and the other is charge neutral. The resonance makes the structure symmetric on both beads for blue dye. All non-bonded 1j potentials are used based on the default Martini force fields 2.0.

Since there are no established CG models for red 40 and blue 1 molecule, the validations of the CG models for both dyes are based on comparing the experimental partitioning coefficients log D with calculated log D in the simulation. However, the CG models could not be adjusted for both dyes to match the experimental log D values and the experimental phenomenon. The difference was reconciled by adopting the CG models for both dyes based on matching the selective molecular recognition that happened in the previous study instead of matching the experimental log values. One explanation of not choosing to match the conventional validation of log D values is that here CTAB plays an important role in the selective partitioning experiments. The conventional validation of the CG models doesn't include CTAB as one component, which might lead to the inconsistency between the simulations and experiments.

MD of CTAB Dependent Selective Partitioning

FIGS. 20A-20D show frames from simulations of CTAB dependent dye partitioning into the octanol phase. Initial structures had mixtures of dyes at a 1:1 ratio in the water. Upon equilibration the dyes transferred into the octanol with the amount of each dye depending on the CTAB concentration. In FIG. 20A, when the CTAB concentration is low, the red dye partitions into the octanol phase. When the CTAB concentration is increased (FIGS. 20B-20D), the number of red dye molecules in the octanol phase increases. From the simulations, insights can be obtained into possible structural mechanisms. For instance, when the CTAB concentration was relatively high in FIG. 20D, CTAB formed a multilayer phase at the water-octanol interface, and this multilayer phase trapped more red dye than blue dye shown.

Thus, the mechanism involved in the selectivity of dyes dependent on CTAB concentration is that the multilayer phase formed at the water-octanol interface prevents the red dye from crossing the interface into the octanol phase, which allows blue dyes going into the octanol phase. This mechanism is consistent with the experiments shown in FIGS. 18A-18E. When CTAB concentration is high, there is a bright birefringence ring around the droplet under the cross-polarized microscope when red dye is present no matter if it is pure red or it is a mixture with red and blue dye. Such birefringence is to be expected from a lamellar phase which has different refractive indices in different directions. (Thornburg, 1957.) There is no noticeable birefringence ring around the droplet under the cross-polarized microscope when only pure blue dye is present.

The MD simulation results are qualitatively consistent with experimental observations in the following ways. First, red appeared to be favored in the octanol at low CTAB concentration, while at higher CTAB concentrations blue dye entered that phase. Second, at higher CTAB concentrations, red dye appeared trapped in a lamellar phase that forms from CTAB at the interface. However, there are several quantitative differences between the simulation and experiment. First, both dye and CTAB concentrations used in the simulations are much higher than in the experiments. In the simulation, 100 CTAB molecules were treat in 10000 octanol molecules as the low concentration, but the calculated CTAB concentration is 60 mM in this case. Additionally, there is no situation where excess dye remains in the water, as was the case in experiments in FIGS. 17A-17C even though both dyes concentrations are much higher than experiment. However, when one considers the surface area to volume ratios of the interface, these differences are understandable. For instance, the surface area to volume ratio is $10^5$ times higher in the simulation than in the experiment. Both CTAB and the two dye molecules adsorb to the interface in the simulations. This molecular absorption at the interface is also expected in the experiments, but because there are so many molecules available from the bulk water and octanol phases it does not significantly reduce the concentrations in the bulk. It demonstrates that in experiments, there were enough molecules including dyes and CTAB to cover the interface but in MD simulations, due to the small simulation box size limitations compared with experimental length scale, there were not enough molecules to cover the interface. Such differences in concentrations due to surface area to volume ratios were common in simulations of interfaces.

FIGS. 21A-21C show the spatial distribution of the 5 different molecules (octanol, water, CTAB, red dye, blue dye) along the z axis of the simulation. From FIG. 21B, it can be seen that when there are 1000 CTAB in octanol, which is the highest CTAB concentration that was used in the simulations, there were two peaks at the interface, which indicates the formation of a lamellar phase at the interface. From FIG. 21C, it can be seen that when CTAB concentration is low, there is more blue dye than red dye at the interface. However, when CTAB concentration keeps increasing, there was more red dye at the interface than blue dye. And the lamellar phase is observed at the interface when there is much more red dye at the interface than blue dye.

Some differences between MD simulation results and this proposed mechanism, as shown in FIGS. 23A-23C, are that since blue dye partitioning into octanol when the CTAB concentration was high was a kinetic effect, red dye was thermodynamically favored in octanol phase after the system is equilibrated. However, the MD simulation showed that the blue dye was favored in octanol phase at high CTAB concentration shown in FIG. 20D, which is expected to be long enough to reach equilibrium. The discrepancy between the experiment and MD simulation can be explained by the length scale between the experiment and simulation. The difference in surface area to volume ratios between the simulation and experiment, reconcile this inconsistency. Since the surface area to volume ratio is $10^5$ times higher in the simulation than in the experiment, it is consistent with the MD simulations above showing that there is no dye left in water. When the CTAB concentration is high, red dye is trapped by CTAB bilayers at the interface and due to the surface area to volume ratio effect, there will not be enough red dye partitioning into octanol phase in order to be consistent with experiments showing red dye is thermodynamically favored, such that MD simulation only shows the kinetic effect of blue partitioning into octanol phase after a relatively long running time.

Another discrepancy between the MD simulations and experiments was that the ratio of red dye to blue dye concentration in MD simulations was 1:1, which is different from the experimental 8:1 ratio. The reason the experiments used 8:1 ratio of red dye to blue dye concentration is that blue dye has higher extinction coefficients which means that blue dye is much brighter than red dye when both dyes have the same concentration. In order to have both dyes showing the similar brightness that can be detected by the microscope, the experiments chose 8:1 ratio. However, in MD simulations, there is no technical issue involved using 1:1 ratio of red and blue dye concentration. Additionally, due to the surface area to volume ratio effect, there might be not enough blue dye to saturate the interface if using 8:1 ratio. The 1:1 ratio of red and blue dye concentration was chosen in order to compare the selective partitioning at different CTAB concentrations fairly. Although there are quantitative discrepancies, the qualitative trends are consistent with the experiments. The main contribution of CG-MD simulations here is to provide structural insights into the mechanism of the selectivity based on the gradually increasing CTAB concentrations.

Mechanism of CTAB-Dependent Molecular Recognition

The observation of a lamellar CTAB phase at the interface in the simulations that binds or sequesters red dye, but not blue dye suggests a mechanism for the CTAB dependent partitioning. That is, red dye may get trapped in this interfacial layer and not transfer into the bulk, while the blue dye can cross it more quickly leading to more dye observed in the bulk octanol. In order to test this hypothesis similar system was simulated with red dye only FIG. 22A and blue dye only FIG. 22B at the high CTAB concentration used in FIG. 20D. From FIG. 22A, it was noted that red dyes have been trapped at the multilayer phase formed by high CTAB concentration at the water-octanol interface. However, from FIG. 22B, it was noted that no blue dye had been trapped at the multilayer phase formed by high CTAB concentration at the water-octanol interface. This was consistent with the hypothesis that the multilayer phase formed at high CTAB concentration prevents the red dye from partitioning into the octanol phase, which allows blue dyes to partition into the octanol phase first. FIG. 22C shows quantitative analysis from the simulation indicating that significantly more red dye than blue dye are trapped at the interface formed by the CTAB lamellar phase.

Based on the experimental observations and MD simulations shown here, the mechanism for CTAB dependent selectivity illustrated in FIGS. 23A-23C was proposed. When the CTAB concentration is low (FIG. 23A), no lamellar phase is observed at the water and octanol interface. The formation of CTAB-red dye reversed micelles with two CTAB molecules per dye molecule in the octanol phase was thermodynamically favored, resulting in selective extraction of the red dye from the aqueous phase.

When the CTAB concentration was high and in excess of available dye (FIG. 23C) a thick lamellar phase formed at the interface that binds the red dye and slows its partitioning into the bulk octanol phase. The blue dye however was able to cross the selectively permeable lamellar phase more quickly. Since there is enough CTAB to extract all dyes, all dye is eventually extracted into octanol phase. At intermediate CTAB concentrations (FIG. 23B), CTAB forms a temporary lamellar phase at the water-octanol interface. The multilayer phase initially prevents red dye from partitioning into the octanol phase resulting in faster blue partitioning. However, as the dye:CTAB ratio in the octanol increases, dye molecules at the interface are depleted and the lamellar phase eventually dissipates. The red dye then is able to cross the interface and replaces the blue dye to reach an equilibrium with only red dye in the octanol. The lamellar phase that forms at the water-octanol interface appears to be highly selective for binding of the red dye instead of blue dye. Therefore, the aggregation layer is considered a dynamic supramolecular aptamer. The formation of lipid mesophases plays many roles in biology, most notably in the formation of cell membranes, (Alireza, 2008; Javanainen, 2021) but also lipid droplets (Mahamid, 2019) and drug delivery (Streck, 2016). Results indicate that aggregation of small molecules can also result in the selective of partitioning molecules.

Conclusions

Both thermodynamic and kinetic aspects to the CTAB-mediated molecular recognition of the red and blue dyes were studied herein. The red dye appeared to be thermodynamically favored to partition into the octanol phase when CTAB was present, where it formed micelles composed of two CTAB molecules per dye molecule in order to balance the charge. At low CTAB concentration, where the number of CTAB molecules were limited relative to the dyes, a selective partitioning for the red dye was observed. The selectivity for blue dye observed at higher CTAB concentrations appeared to be due to a kinetic mechanism, where the blue dye was able to transfer across the interface at a faster rate than the red dye. This was due to the formation of a supramolecular structure at the interface that sequestered the red dye and prevented it from diffusing further into the drop, while the blue dye was able to cross the structure. This structure was referred to as a supramolecular aptamer. CG-MD simulations have demonstrated this structure as supramolecular aptamer clearly and elucidated both thermodynamic and kinetic mechanisms at different CTAB concentrations at a molecular level. This mechanism has implications for molecular recognition in biology. Since the concentration of just a single surfactant can regulate the selectivity of two dyes between the aqueous and organic phase, the idea that various lipid compositions might act as aptamers would provide a new mechanism of molecular recognition beyond that of covalent polymers such as protein. For instance, the lipid composition of a lipid bilayer or droplet could lead to selective partitioning of other molecules which may trigger or regulate signal cascades. (Lowry, 2023.) This is a different way of thinking about lipids in which supramolecular combinations of small molecules could form a receptor that might couple molecular recognition to cell signaling events. As the possible combinations of lipids in a mixture are comparable in number to the number of possible protein sequences (Bell, 2020) this perspective can provide new lipid-based targets analogous to protein targets. Such mechanisms could explain how lipid nanoparticles are capable of targeting specific tissues and cells without any targeting ligands. (Sago, 2018.) Lipid trafficking might also be understood in terms of lipids trafficking proteins rather than the other way around. Applications of this idea could lead to antibody free biosensors as well as new bioinspired chemical processes.

Experimental Methods

Organic Phase Preparation

The cetyltrimethylammonium bromide (CTAB) was purchased from Sigma-Aldrich (St. Louis, USA). CTAB was dissolved in 1-octanol to make solutions with concentrations of 60, 30, 15, 7.5, and 3.75 mM.

Aqueous Phase Preparation

Erioglaucine disodium salt (Blue 1) was purchased from Sigma-Aldrich (St. Louis, MO, USA). Allura red AC (Red 40) was obtained from TCI (Tokyo, Japan). For the birefringent ring experiments shown in FIG. 3, 400 uM red 40 dye and 50 uM blue 1 dye were dissolved in D.I. water. For the equilibrium tube experiment, dye concentrations were chosen based on the assumption that one dye molecule can be sequestered for every two CTAB molecules. The dye concentrations are chosen such that once this criterion is met, there will be enough dye left in the aqueous phase to be detected by a spectrophotometer so that the aqueous phase solution will have concentrations of 1700 uM, 850 uM, 425 uM, 213 uM, 106 uM for both red 40 dye and blue 1 dye.

Equilibrium Tubes Set-Up

For sample preparation and mixing, 50 mL centrifuge tubes were used. 1 mL of the appropriate organic solution and 10 mL of the appropriate aqueous solution were added to each tube. Solutions were allowed to equilibrate on a shaker for 14 days and then were centrifuged and transferred to 15 mL centrifuge tubes for pictures.

Microarrays and Flow Cell Assembly

The different lipid solutions were microarrayed using 0.1-10 μL disposable sterile pipet tips (VWR) directly onto the substrate. Drops were 0.1 uL in volume and only had contact with the bottom glass slide. After tapping the microarray onto the substrate, 0.3 mm thick PDMS was used as a spacer between the substrate and the cover. The two spacers will be fixed 1.8 cm apart onto the substrate. The coverslip will be placed carefully onto two spacers. Microscope slides manufactured by Azer Scientific (Unifrost) will be used as substrates. Microscope cover glasses (25 mm Å~25 mm) manufactured by VWR will be used as slipcovers. Approximately 130 μL of aqueous solution was added to the right side of the flow cell and moved quickly through the flow cell. Prior to experiments, test samples will be incubated in 1 mL of deionized water to test for stability.

Data Analysis

A nanodrop spectrophotometer was used to determine the concentrations of dye in the aqueous phase at equilibrium using the UV-vis pre-set mode. The blue 1 dye and red 40 dye used wavelengths of 629 nm and 501 nm respectively for absorbance measurements. Microarray samples requiring 30 min or less were imaged with a digital microscope (Dino-Lite Pro2 AD-413T or Dino-Lite Edge AM4115ZT) at 100 Å~ magnification. For imaging lipid microarrays, a portable backlight stage (Dino-Lite MSBL-ZW1R) was used as a white light source and positioned under the bottom of the slide to illuminate the sample.

Computational Methods

Simulation of Calculating Log D for Blue and Red Dye

LAMMPS (Thompson, 2022) open-source software has been used to perform all the MD simulations. The time step is 30 fs, and 1.2 nm cut-off radius was used for all non-bonded interactions including Lennard-Jones potential as well as electrostatic interactions. And all the non-bonded interactions were calculated by means of a particle-particle particle-mesh (pppm) with an accuracy of $10^{-3}$ in LAMMPS. The running simulation time is around 1 microsecond. The total number of CG particles used in simulation is around 40,000. Periodic boundary conditions are applied in all the MD simulations.

In order to verify that the Martini coarse graining model is appropriate for the blue and red dye, force field modifications have been conducted iteratively for the CG models such that the simulated log D values match the experimental log D values. Since the experimental values of log Dow for blue and red dye are not available, log D was measured for blue and red dye through experiments shown in supporting information.

In order to compute log D directly, the free energies of solvation are both considered in water and octanol phases. Based on the equation (Cesar, 2009)

$$\Delta\Delta G_{ow} = \Delta G_w - \Delta G_o = -\ln 10 \, kT \log D_{ow} \quad (1)$$

Note that $\Delta G_w$ and $\Delta G_o$ are the free energy difference of solvation in water and octanol phase, respectively. Here the water phase includes 1000 CG water molecules, and the octanol phase includes 25 CG water molecules and 450 CG octanol molecules which is water-saturated octanol phase (Best, 1999). $\Delta G_w$ and $\Delta G_o$ as the free energy difference were calculated through the solute in vacuum (state A) and in the condensed phase (water/octanol) using the finite-difference thermodynamic integration (FDTI) approach (Berendson, 1987):

$$\Delta G_{BA} = G_B - G_A = \int_{\lambda_A}^{\lambda_B} \left( \frac{\partial U(\lambda)}{\partial \lambda} \right)_\lambda d\lambda \quad (2)$$

$$\Delta G_w = \Delta G_{BA}(B = W) \text{ and } \Delta G_o = \Delta G_{BA}(B = O) \quad (3)$$

Note that $\lambda$ is a coupling parameter with value ranging from 0 to 1. $U(\lambda)$ denotes the potential energy between the solute and solvent, here the potential energy includes the van der Waals as well as electrostatic interactions. When $\lambda=0$, which denotes that the solute is in vacuum (no solvent). When $\lambda=1$, which denotes that the solute is in the condensed phase (water or octanol). Through FDTI approach, the calculations of $\Delta G_w$ and $\Delta G_o$ can be obtained through the command of "compute fep" in LAMMPS. Log D can be calculated through equation (1).

Simulation of Switch Selectivity of Blue and Red Dyes in Water/Octanol/CTAB System The modeling structure contains aqueous phase with two dyes (10000 CG water molecules, 60 red dyes and 60 blue dyes) as well as organic phase (10000 CG octanol molecules, the number of CG CTAB molecules varies from 0~1000). NPT was performed at approximately 1 microsecond with constant particle number and constant pressure. The temperature used here is 300K, and the pressure is 1 bar, isotropic along three directions. The box size after NPT is ~13.2×12.0×27.0 $nm^3$.

Other advantages which are obvious, and which are inherent to the invention, will be evident to one skilled in the art. It will be understood that certain features and sub-combinations are of utility and may be employed without reference to other features and sub-combinations. This is contemplated by and is within the scope of the claims. Since many possible embodiments may be made of the invention without departing from the scope thereof, it is to be understood that all matter herein set forth or shown in the accompanying drawings is to be interpreted as illustrative and not in a limiting sense.

REFERENCES LISTED

Zhong, C., Hu, C., Kumar, R., Trouillet, V., Biedermann, F., & Hirtz, M. (2021). Cucurbit [n] uril-Immobilized Sensor Arrays for Indicator-Displacement Assays of Small Bioactive Metabolites. ACS Applied Nano Materials.

Bajerski, F., Stock, J., Hanf, B., Darienko, T., Heine-Dobbernack, E., Lorenz, M., . . . & Overmann, J. (2018). ATP content and cell viability as indicators for cryostress across the diversity of life. Frontiers in physiology, 9, 921.

Tian, S., Tian, Z., Yang, H., Yang, M., & Zhang, Y. (2017). Detection of viable bacteria during sludge ozonation by the combination of ATP assay with PMA-Miseq sequencing. Water, 9(3), 166.

Crouch, S. P. M., Kozlowski, R., Slater, K. J., & Fletcher, J. (1993). The use of ATP bioluminescence as a measure of cell proliferation and cytotoxicity. Journal of immunological methods, 160(1), 81-88.

Herrera, B. T., Moor, S. R., McVeigh, M., Roesner, E. K., Marini, F., & Anslyn, E. V. (2019). Rapid optical determination of enantiomeric excess, diastereomeric excess, and total concentration using dynamic-covalent assemblies: A demonstration using 2-aminocyclohexanol and chemometrics. Journal of the American Chemical Society, 141(28), 11151-11160.

Sedgwick, A. C., Brewster, J. T., Wu, T., Feng, X., Bull, S. D., Qian, X., . . . & Sun, X. (2021). Indicator displacement assays (IDAs): the past, present and future. Chemical Society Reviews.

Mitchell, L., New, E. J., & Mahon, C. S. (2021). Macromolecular Optical Sensor Arrays. ACS Applied Polymer Materials, 3(2), 506-530.

Zhang, H., Ji, X., Li, P., Liu, C., Lou, J., Wang, Z., . . . & Zhu, X. (2020). Liquid-liquid phase separation in biology: mechanisms, physiological functions and human diseases. Science China Life Sciences, 63(7), 953-985.

Peng, L., Li, E. M., & Xu, L. Y. (2020). From start to end: phase separation and transcriptional regulation. Biochimica et Biophysica Acta (BBA)-Gene Regulatory Mechanisms, 194641.

O'Flynn, B. G., & Mittag, T. (2021). The role of liquid-liquid phase separation in regulating enzyme activity. Current Opinion in Cell Biology, 69, 70-79.

Alberti, Simon. "Phase separation in biology." Current Biology 27.20 (2017): R1097-R1102.

Hyman, Anthony A., Christoph A. Weber, and Frank Jülicher. "Liquid-liquid phase separation in biology." Annual review of cell and developmental biology 30 (2014): 39-58.

Blaker, Jonny J., Jonathan C. Knowles, and Richard M. Day. "Novel fabrication techniques to produce microspheres by thermally induced phase separation for tissue engineering and drug delivery." Acta biomaterialia 4.2 (2008): 264-272.

Boeynaems, Steven, et al. "Protein phase separation: a new phase in cell biology." Trends in cell biology 28.6 (2018): 420-435.

Entezari, Mohammad Hassan, and A. Keshavarzi. "Phase-transfer catalysis and ultrasonic waves II: saponification of vegetable oil." Ultrasonics Sonochemistry 8.3 (2001): 213-216.

Bell, Tracey N., Keke Feng, Gabriel Calvin, David H. Van Winkle, and Steven Lenhert. "Organic Composomes as Supramolecular Aptamers." ACS Omega 2020 5(42), 27393-27400.

Rowland, Malcolm, and Shaikh B. Matin. "Kinetics of drug-drug interactions." Journal of Pharmacokinetics and Biopharmaceutics L6 (1973): 553-567.

Zeyda, Maximilian, et al. "LAT displacement from lipid rafts as a molecular mechanism for the inhibition of T cell signaling by polyunsaturated fatty, acids." Journal of Biological Chemistry 277.32 (2002): 28418-28423.

Yan, Z.; Wang, J., Specificity quantification of biomolecular recognition and its implication for drug discovery. Sci Rep 2012, 2, 309.

Vazquez, M. E.; Caamano, A. M.; Mascarenas, J. L., From transcription factors to designed sequence-specific DNA-binding peptides. Chem Soc Rev 2003, 32 (6), 338-49.

Bender, R. E. B. a. S. L., Molecular Recognition of Protein-Ligand Complexes Applications to Drug Design. Chem. Rev. 1997, 97, 1359-1472.

P. Zhou*, J. Huang and F. Tian*, Specific Noncovalent Interactions at Protein-Ligand Interface: Implications for Rational Drug Design. Current Medicinal Chemistry 2012, 19, 226-238.

Bell, T. N.; Feng, K.; Calvin, G.; Van Winkle, D. H.; Lenhert, S., Organic Composomes as Supramolecular Aptamers. ACS Omega 2020, 5 (42), 27393-27400.

D Segré, D. B.-E., D W Deamer, D Lancet, The lipid world. Origins of Life and Evolution of the Biosphere 2001, 31, 119-145.

Kahana, A.; Maslov, S.; Lancet, D., Dynamic lipid aptamers: non-polymeric chemical path to early life. Chem Soc Rev 2021, 50 (21), 11741-11746.

Kahana, A.; Lancet, D., Self-reproducing catalytic micelles as nanoscopic protocell precursors. Nature Reviews Chemistry 2021, 5 (12), 870-878.

Klein, I. A.; Boija, A.; Afeyan, L. K.; Hawken, S. W.; Fan, M.; Dall'Agnese, A.; Oksuz, O.; Henninger, J. E.; Shrinivas, K.; Sabari, B. R.; Sagi, I.; Clark, V. E.; Platt, J. M.; Kar, M.; McCall, P. M.; Zamudio, A. V.; Manteiga, J. C.; Coffey, E. L.; Li, C. H.; Hannett, N. M.; Guo, Y. E.; Decker, T. M.; Lee, T. I.; Zhang, T.; Weng, J. K.; Taatjes, D. J.; Chakraborty, A.; Sharp, P. A.; Chang, Y. T.; Hyman, A. A.; Gray, N. S.; Young, R. A., Partitioning of cancer therapeutics in nuclear condensates. Science 2020, 368 (6497), 1386-1392.

Hilt, J. Z.; Byrne, M. E., Configurational biomimesis in drug delivery: molecular imprinting of biologically significant molecules. Adv Drug Deliv Rev 2004, 56 (11), 1599-620.

Yang, F.; Zuo, X.; Fan, C.; Zhang, X.-E., Biomacromolecular nanostructures-based interfacial engineering: from precise assembly to precision biosensing. National Science Review 2018, 5 (5), 740-755.

Senthamizh Selvi, R., Nanthini, R and Sukanyaa, G, The Basic Principle of Phase-Transfer Catalysis, Some Mechanistic Aspects and Important Applications. International Journal of Scientific & Technology Research 2012, 1 (3), 61-63.

Makosza, M. F., Michal, Phase Transfer Catalysis—Basic Principles, Mechanism and Specific Features. Current Catalysis 2012, 1 (2), 79-87(9).

Makosza, M., Phase-transfter catalysis. A general green methodology in organic synthesis. Pure and Applied Chemistry 2000, 72 (7), 1399-1403.

Godha, A. K.; Thiruvengadam, J.; Abhilash, V.; Balgi, P.; Narayanareddy, A. V.; Vignesh, K.; Gadakh, A. V.; Sathiyanarayanan, A. M.; Ganesh, S., Environmentally benign nucleophilic substitution reaction of arylalkyl halides in water using CTAB as the inverse phase transfer catalyst. New Journal of Chemistry 2019, 43 (40), 16041-16045.

Szostak, A. D. E. J. W., In vitro selection of RNA molecules that bind specific ligands Nature 1990, 346.

Richard H. Henchman, H.-L. W., Steven M. Sine, Palmer Taylor, and J. Andrew McCammon, Asymmetric Structural Motions of the Homomeric a7 Nicotinic Receptor Ligand Binding Domain Revealed by Molecular Dynamics Simulation. Biophysical Journal 2003, 85, 3007-3018.

Andrei A. Ivanov, I. F., T. Kendall Harden, Kenneth A. Jacobson, Molecular dynamics simulation of the P2Y$_{14}$ receptor. Ligand docking and identification of a putative binding site of the distal hexose moiety. Bioorganic & Medicinal Chemistry Letters 2006, 17 (3), 761-766.

Rakers, C.; Bermudez, M.; Keller, B. G.; Mortier, J.; Wolber, G., Computational close up on protein-protein interactions: how to unravel the invisible using molecular dynamics simulations? Wiley Interdisciplinary Reviews: Computational Molecular Science 2015, 5 (5), 345-359.

Reynwar, B. J.; Deserno, M., Membrane composition-mediated protein-protein interactions.

Chavent, M.; Duncan, A. L.; Sansom, M. S., Molecular dynamics simulations of membrane proteins and their interactions: from nanoscale to mesoscale. Curr Opin Struct Biol 2016, 40, 8-16.

Pluhackova, K.; Kirsch, S. A.; Han, J.; Sun, L.; Jiang, Z.; Unruh, T.; Bockmann, R. A., A Critical Comparison of Biomembrane Force Fields: Structure and Dynamics of Model DMPC, POPC, and POPE Bilayers. J Phys Chem B 2016, 120 (16), 3888-903.

Zhuang, X.; Davila-Contreras, E. M.; Beaven, A. H.; Im, W.; Klauda, J. B., An extensive simulation study of lipid bilayer properties with different head groups, acyl chain lengths, and chain saturations. Biochim Biophys Acta 2016, 1858 (12), 3093-3104.

Kikkawa, N.; Ishiyama, T.; Morita, A., Molecular dynamics study of phase transfer catalyst for ion transfer through water—chloroform interface. Chemical Physics Letters 2012, 534, 19-22.

James L. Melville, K. R. J. L., Claire Wilson, Bryan Allbutt, Edmund K. Burke, Barry Lygo, and Jonathan D. Hirst, Exploring Phase-Transfer Catalysis with Molecular Dynamics and 3D/4D Quantitative Structure-Selectivity Relationships. J. Chem. Inf. Model 2005, 45, 971-981.

Oberbrodhage, J., Phase transfer catalysts between polar and non-polar media: a molecular dynamics simulation of tetrabutylammonium iodide at the formamide/hexane interface. *Phys. Chem. Chem. Phys.* 2000, 2, 129-135.

Jang, C.; Abrams, C. F., Thermal and mechanical properties of thermosetting polymers using coarse-grained simulation. *The European Physical Journal Special Topics* 2016, 225 (8-9), 1775-1783.

Cesar A. López, A. J. R., Alex H. de Vries, Lubbert Dijkhuizen, Philippe H. Hünenberger, and Siewert J. Marrink, Martini Coarse-Grained Force Field: Extension to Carbohydrates. J. Chem. Theory Comput. 2009, 5, 3195-3210.

Siewert J. Marrink, H. J. R., Serge Yefimov, D. Peter Tieleman, and Alex H. de Vries, The MARTINI Force Field: Coarse Grained Model for Biomolecular Simulations. *J. Phys. Chem. B* 2007, 111, 7812-7824.

Lin, S.; Zhang, J.; Strano, M. S.; Blankschtein, D., Understanding selective molecular recognition in integrated carbon nanotube-polymer sensors by simulating physical analyte binding on carbon nanotube-polymer scaffolds. *Soft Matter* 2014, 10 (32), 5991-6004.

Uusitalo, J. J.; Ingolfsson, H. I.; Akhshi, P.; Tieleman, D. P.; Marrink, S. J., Martini Coarse-Grained Force Field: Extension to DNA. *J Chem Theory Comput* 2015, 11 (8), 3932-45.

Uusitalo, J. J.; Ingolfsson, H. I.; Marrink, S. J.; Faustino, I., Martini Coarse-Grained Force Field: Extension to RNA. *Biophys J* 2017, 113 (2), 246-256.

Luca Monticelli, S. K. K., Xavier Periole, Ronald G. Larson, D. Peter Tieleman, and Siewert-Jan Marrink, The MARTINI Coarse-Grained Force Field: Extension to Proteins. *J. Chem. Theory and Comput.* 2008, 4, 819-834.

Alessandri, R.; Barnoud, J.; Gertsen, A. S.; Patmanidis, I.; de Vries, A. H.; Souza, P. C. T.; Marrink, S. J., Martini 3 Coarse-Grained Force Field: Small Molecules. *Advanced Theory and Simulations* 2021, 5 (1).

Marlon J. Hinner, S.-J. M., and Alex H. de Vries, Location, Tilt, and Binding: A Molecular Dynamics Study of Voltage-Sensitive Dyes in Biomembranes. *J. Phys. Chem. B* 113, 15807-15819.

Resonance. *IUPAC-compendium-of-chemical-terminology* (*the Gold Book*) 2006, *Online corrected version.*

Thornburg, W., The form birefringence of lamellar systems containing three or more components. *The Journal of biophysical and biochemical cytology* 1957, 3.3, 413.

Alireza Mashaghi, M. S., Jonathan Popplewell, Marcus Textor,† and Erik Reimhult, Optical Anisotropy of Supported Lipid Structures Probed by Waveguide Spectroscopy and Its Application to Study of Supported Lipid Bilayer Formation Kinetics. *Anal. Chem.* 2008, 80, 3666-3676.

Javanainen, M.; Martinez-Seara, H.; Kelly, C. V.; Jungwirth, P.; Fabian, B., Anisotropic diffusion of membrane proteins at experimental timescales. *J Chem Phys* 2021, 155 (1), 015102.

Mahamid, J.; Tegunov, D.; Maiser, A.; Arnold, J.; Leonhardt, H.; Plitzko, J. M.; Baumeister, W., Liquid-crystalline phase transitions in lipid droplets are related to cellular states and specific organelle association. *Proc Natl Acad Sci USA* 2019, 116 (34), 16866-16871.

Streck, L.; Sarmento, V. H.; Machado, P. R.; Farias, K. J.; Fernandes-Pedrosa, M. F.; da Silva-Junior, A. A., Phase Transitions of Isotropic to Anisotropic Biocompatible Lipid-Based Drug Delivery Systems Overcoming Insoluble Benznidazole Loading. *Int J Mol Sci* 2016, 17 (7).

Lowry, T. W.; Kusi-Appiah, A. E.; Fadool, D. A.; Lenhert, S., Odor Discrimination by Lipid Membranes. *Membranes* 2023, 13 (2).

Sago, C. D.; Lokugamage, M. P.; Islam, F. Z.; Krupczak, B. R.; Sato, M.; Dahlman, J E, Nanoparticles That Deliver RNA to Bone Marrow Identified by in Vivo Directed Evolution. *J Am Chem Soc* 2018, 140 (49), 17095-17105.

Thompson, A. P.; Aktulga, H. M.; Berger, R.; Bolintineanu, D. S.; Brown, W. M.; Crozier, P. S.; in't Veld, P. J.; Kohlmeyer, A.; Moore, S. G.; Nguyen, T. D.; Shan, R.; Stevens, M. J.; Tranchida, J.; Trott, C.; Plimpton, S. J., LAMMPS—a flexible simulation tool for particle-based materials modeling at the atomic, meso, and continuum scales. *Computer Physics Communications* 2022, 271.

Scott A. Best, K. M. M., Jr., and Charles H. Reynolds, Free Energy Perturbation Study of Octanol/Water Partition Coefficients: Comparison with Continuum GB/SA Calculations. *J. Phys. Chem. B* 1999, 103, 714-726.

Berendsen, W. F. v. G. a. H. J. C., Thermodynamic cycle integration by computer simulation as a tool for obtaining free energy differences in molecular chemistry. *Journal of Computer-Aided Molecular Design.* 1987, 1, 171-176.

What is claimed is:

1. A method of detecting the displacement of a specific analyte, comprising providing an indicator in an organic phase to form a first composition; providing an aqueous phase with a test analyte to form a second composition; adding at least one organic solute to the organic phase; putting the first composition and second composition in contact with each other, thereby forming a lamellar phase and an interface between the first composition and second composition; and detecting the displacement of the indicator in the organic phase, wherein the displacement of the indicator from the organic phase indicates the presence of the specific analyte.

2. The method of claim 1, wherein detecting the analyte further comprises measuring kinetics of the displacement of the analyte.

3. The method of claim 1, further comprising determining analyte concentration based on selective partitioning rate of the indicator and analyte.

4. The method of claim 1, further comprising arraying at least two analytes on a single object; and performing multiplexed detection.

5. The method of claim 1, wherein adding at least one organic solute to the organic phase comprises dissolving the at least one organic solute in the organic phase.

6. The method of claim 1, wherein the analyte comprises small molecules or ions, red color 40, copper, or any combination thereof.

7. The method of claim 1, wherein the organic phase comprises oleic acid, an additive, or any combination thereof.

8. The method of claim 7, wherein the additive comprises phosphonic acid.

9. The method of claim 1, wherein the aqueous phase comprises a biological sample or environmental sample.

10. The method of claim 1, wherein the organic phase has a volume from 1 zeptoliter to 100 milliliters and the aqueous phase has a volume from 100 nanoliters to 500 milliliters.

11. The method of claim 1, further comprising measuring rotation of polarized light.

12. The method of claim 1, wherein the organic phase is in the form of an organic droplet within the aqueous phase.

13. The method of claim 1, wherein the organic solute comprises at least one surfactant.

14. The method of claim 13, wherein the surfactant comprises cetyltrimethylammonium bromide (CTAB).

15. The method of claim 1, wherein detecting the presence of the indicator in the organic phase comprises applying a light source, applying a detector, or any combination thereof.

16. The method of claim 1, wherein the indicator and reagents used are specific for the analyte, so that the indicator is displaced in the presence of the analyte.

17. A biosensor for carrying out the method of claim 1.

18. The biosensor of claim 17, wherein the indicator and reagents used are specific for the analyte, so that the indicator is displaced in the presence of the analyte.

19. The method of claim 1, wherein the method is a carried out using a high throughput assay.

20. The method of claim 1, wherein the method allows for contemporaneous detection of multiple analytes.

* * * * *